US011547351B2

(12) United States Patent
Adachi et al.

(10) Patent No.: US 11,547,351 B2
(45) Date of Patent: Jan. 10, 2023

(54) BODY CONDITION MANAGING DEVICE AND BODY CONDITION MANAGING METHOD

(71) Applicant: Sharp Kabushiki Kaisha, Sakai (JP)

(72) Inventors: Yoshihisa Adachi, Sakai (JP); Rieko Ogawa, Sakai (JP); Yuki Edo, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 103 days.

(21) Appl. No.: 16/624,327

(22) PCT Filed: May 8, 2018

(86) PCT No.: PCT/JP2018/017701
§ 371 (c)(1),
(2) Date: Dec. 19, 2019

(87) PCT Pub. No.: WO2018/235440
PCT Pub. Date: Dec. 27, 2018

(65) Prior Publication Data
US 2020/0129120 A1 Apr. 30, 2020

(30) Foreign Application Priority Data
Jun. 22, 2017 (JP) .............................. JP2017-122612

(51) Int. Cl.
*A61B 5/00* (2006.01)
*G16H 50/20* (2018.01)
*G16H 20/10* (2018.01)

(52) U.S. Cl.
CPC .......... *A61B 5/4848* (2013.01); *A61B 5/7275* (2013.01); *G16H 20/10* (2018.01); *G16H 50/20* (2018.01)

(58) Field of Classification Search
CPC .... A61B 5/4848; A61B 5/7275; G16H 20/10; G16H 50/20
See application file for complete search history.

(56) References Cited

U.S. PATENT DOCUMENTS

| 2005/0010435 A1 | 1/2005 | Kato et al. |
| 2010/0185055 A1 | 7/2010 | Robertson et al. |

(Continued)

FOREIGN PATENT DOCUMENTS

| JP | 3631744 B2 | 3/2005 |
| JP | 2007-188149 A | 7/2007 |

(Continued)

OTHER PUBLICATIONS

Official Communication issued in International Patent Application No. PCT/JP2018/017701, dated Jul. 17, 2018.

*Primary Examiner* — Michael W Kahelin
*Assistant Examiner* — Naveed R. Kolia
(74) *Attorney, Agent, or Firm* — Keating & Bennett, LLP

(57) ABSTRACT

The present invention has an object to manage the manual ingestion (and failure of manual ingestion) of an ingestible object without making the user feel bothered. The present invention includes: a collating unit configured to collate the biological data acquired by a biosensor and the temporal changes of biological data that occur after a medicine is taken and after a medicine is not taken at a medicine-taking timing; and a warning output unit configured to output, on the basis of a result of the collation, information on whether or not a living body has taken the medicine.

8 Claims, 14 Drawing Sheets

(56) References Cited

U.S. PATENT DOCUMENTS

| | | | |
|---|---|---|---|
| 2011/0224912 A1 | 9/2011 | Bhavaraju et al. | |
| 2015/0112208 A1* | 4/2015 | He | A61B 5/02055 600/479 |
| 2016/0188839 A1* | 6/2016 | Kaul | G16H 40/67 705/2 |

FOREIGN PATENT DOCUMENTS

| | | |
|---|---|---|
| JP | 2009-213637 A | 9/2009 |
| JP | 2010-524512 A | 7/2010 |

\* cited by examiner

BODY CONDITION MANAGING DEVICE AND BODY CONDITION MANAGING METHOD

TECHNICAL FIELD

The following disclosure relates to, for example, body condition managing devices.

BACKGROUND ART

Technology has been developed that manages administration of medicines to users. Patent Literature 1 discloses an example of such technology.

The health management system of Patent Literature 1, for example, samples a body fluid from a subject to be examined, checks the health of the subject based on the data obtained from analysis of the body fluid, prepares a medicine to be administered based on results of the health checkup, and optionally administers the prepared medicine to the subject. Additionally, the health management system, if administering a medicine automatically, subsequently stores administration records in a server.

CITATION LIST

Patent Literature

Patent Literature 1: Japanese Patent Application Publication, Tokukou No. 3631744 (registered on Dec. 24, 2004)

SUMMARY OF INVENTION

Technical Problem

If the subject is to take a medicine manually, however, the health management system of Patent Literature 1 requires the subject to manually send administration records to the server, which the subject may find bothersome. In addition, since the subject needs to manually send administration records, the subject may send administration records without actually taking the medicine. The same problems can arise when someone else such as a pharmacy staff member sends administration records on behalf of the subject. If someone else sends administration records, that person needs to take the trouble of asking the subject whether he/she has taken the medicine.

The following disclosure, made in view of these problems, has an object to provide, for example, a body condition managing device capable of managing the manual ingestion of an ingestible object by a living body without making the user feel bothered.

Solution to Problem

To address the problems, the present disclosure, in an aspect thereof, is directed to a body condition managing device connected in a communicable manner to a biological data acquisition unit that acquires biological data representing a condition of a living body, the body condition managing device including: a collating unit configured to collate (1) the biological data acquired by the biological data acquisition unit and (2) a first biological data pattern and a second biological data pattern both being prepared in advance, the first biological data pattern representing temporal drifting of the biological data that occurs after the living body ingests a prescribed ingestible object to be ingested into the living body and the second biological data pattern representing temporal drifting of the biological data that occurs after the living body fails to ingest the ingestible object at a timing at which the living body should ingest the ingestible object; and an output unit configured to output, based on a result of the collation performed by the collating unit, information on whether or not the living body has ingested the ingestible object.

To address the problems, the present disclosure, in another aspect thereof, is directed to a body condition managing method including: the biological data acquisition step of acquiring biological data representing a condition of a living body; the collating step of collating (1) the biological data acquired in the biological data acquisition step and (2) a first biological data pattern and a second biological data pattern both being prepared in advance, the first biological data pattern representing temporal drifting of the biological data that occurs after the living body ingests a prescribed ingestible object to be ingested into the living body and the second biological data pattern representing temporal drifting of the biological data that occurs after the living body fails to ingest the ingestible object at a timing at which the living body should ingest the ingestible object; and the output step of outputting, based on a result of the collation performed in the collating step, information on whether or not the living body has ingested the ingestible object.

Advantageous Effects of Invention

The present disclosure, in an aspect thereof, advantageously enables managing of the manual ingestion of an ingestible object by a living body without making the user feel bothered.

Figure 3:
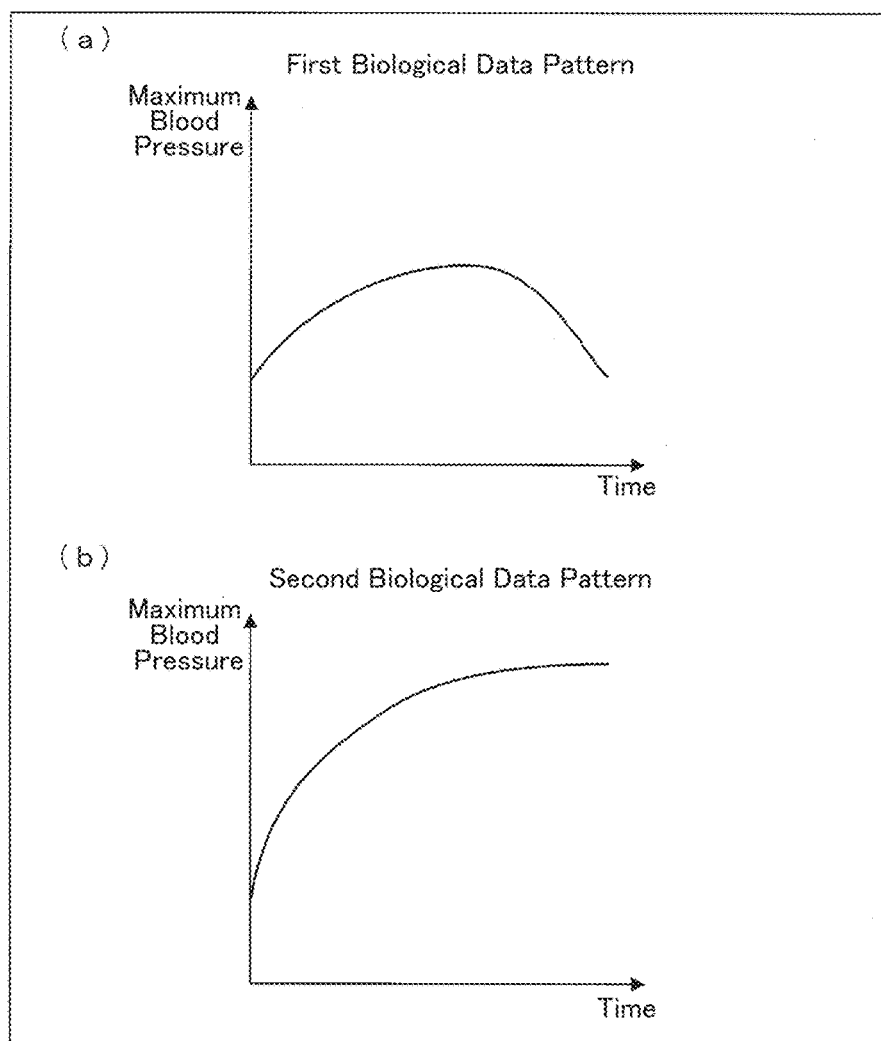

Portion (a) of FIG. 3 is a diagram showing an example first biological data pattern, and (b) of FIG. 3 is a diagram showing an example second biological data pattern.

Figure 4:
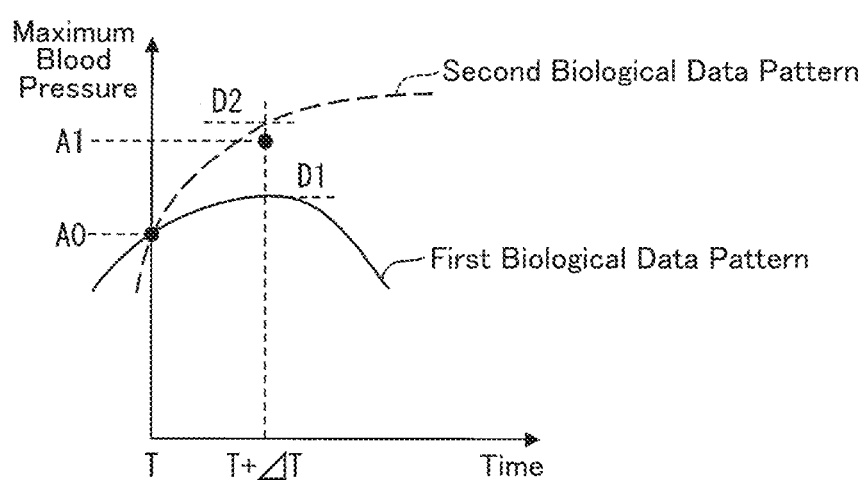

FIG. 4 is a diagram showing an example method of collating biological data and first and second biological data patterns in accordance with Embodiment 1.

Figure 5:
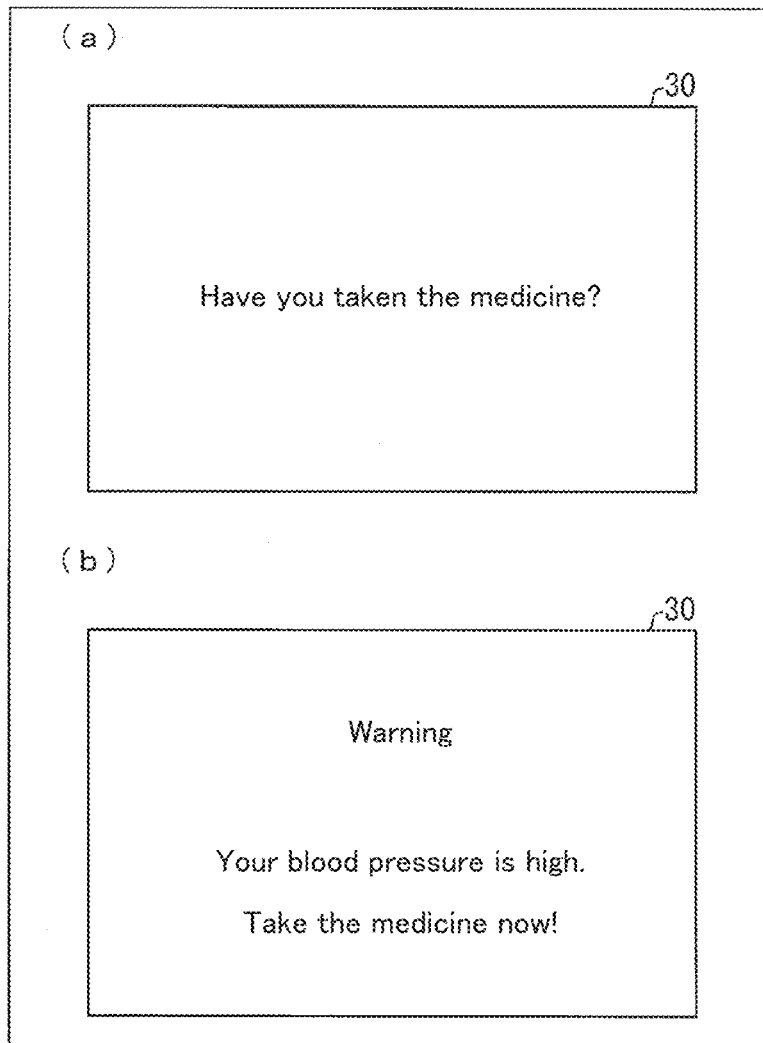

FIG. 5 is an illustration of example warning images being displayed.

Figure 6:
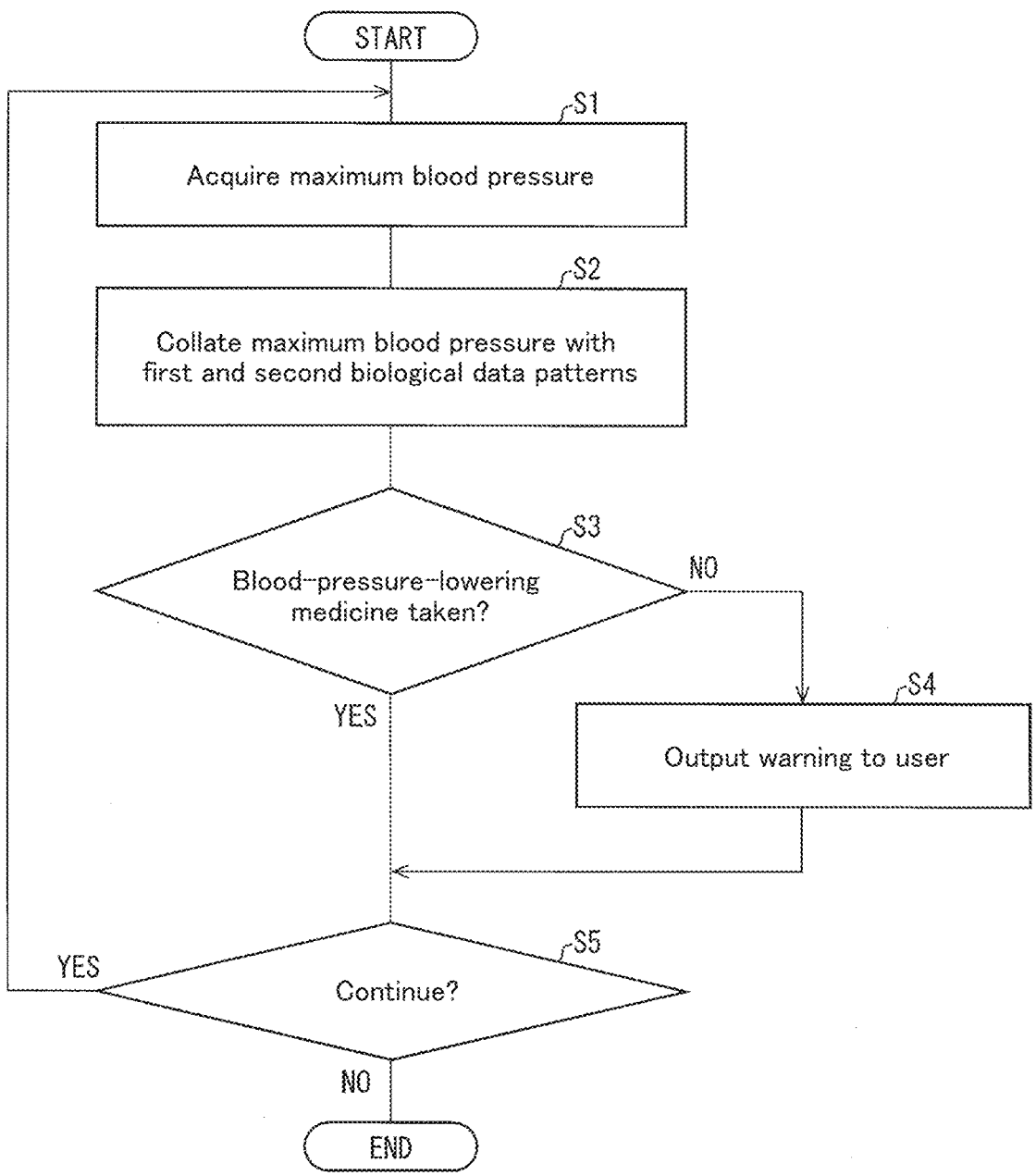

FIG. 6 is a flow chart representing an example medicine-taking managing method in accordance with Embodiment 1.

Figure 7:
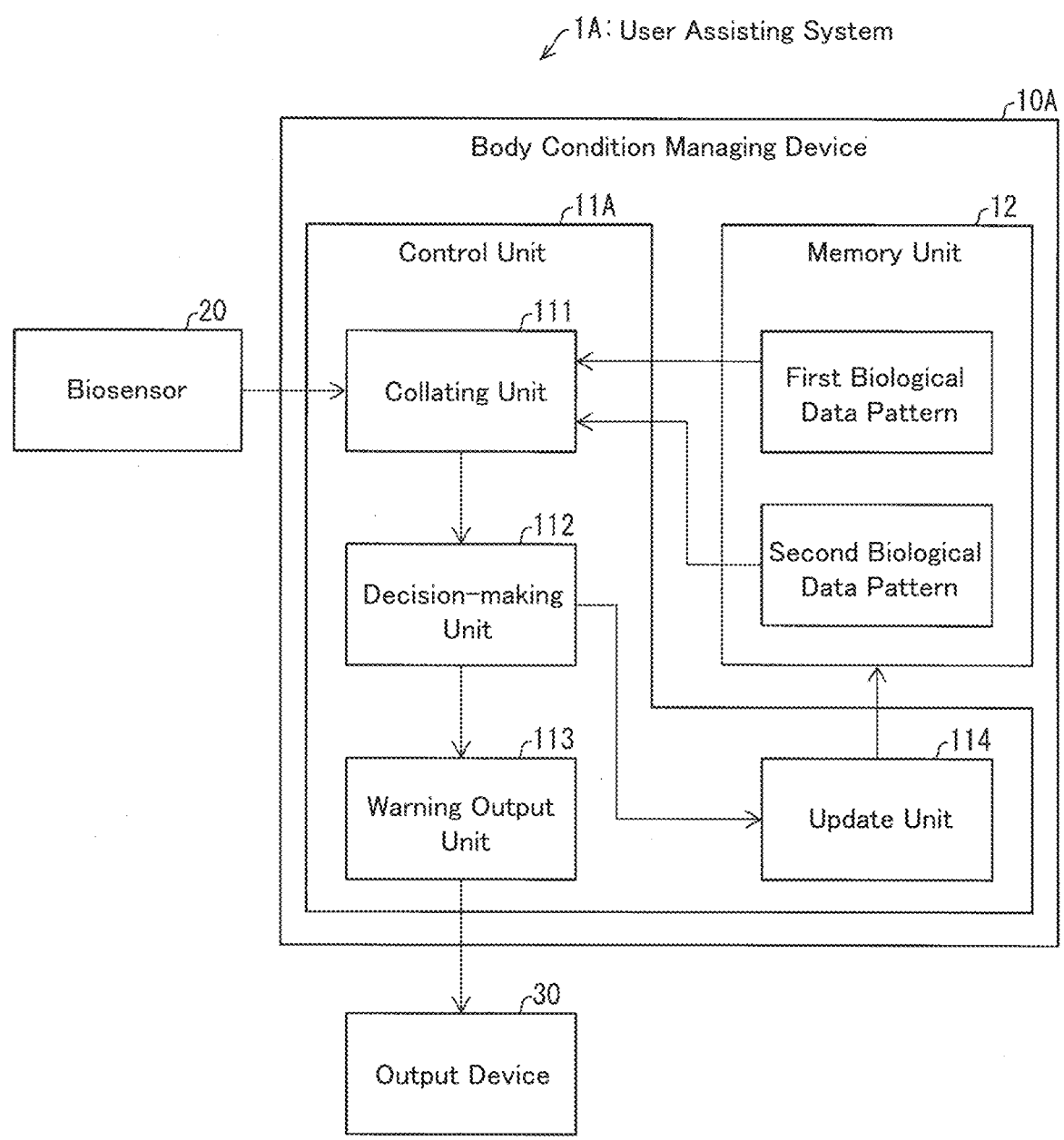

FIG. 7 is a diagram showing an example configuration of a user assisting system in accordance with Embodiment 2.

Figure 8:
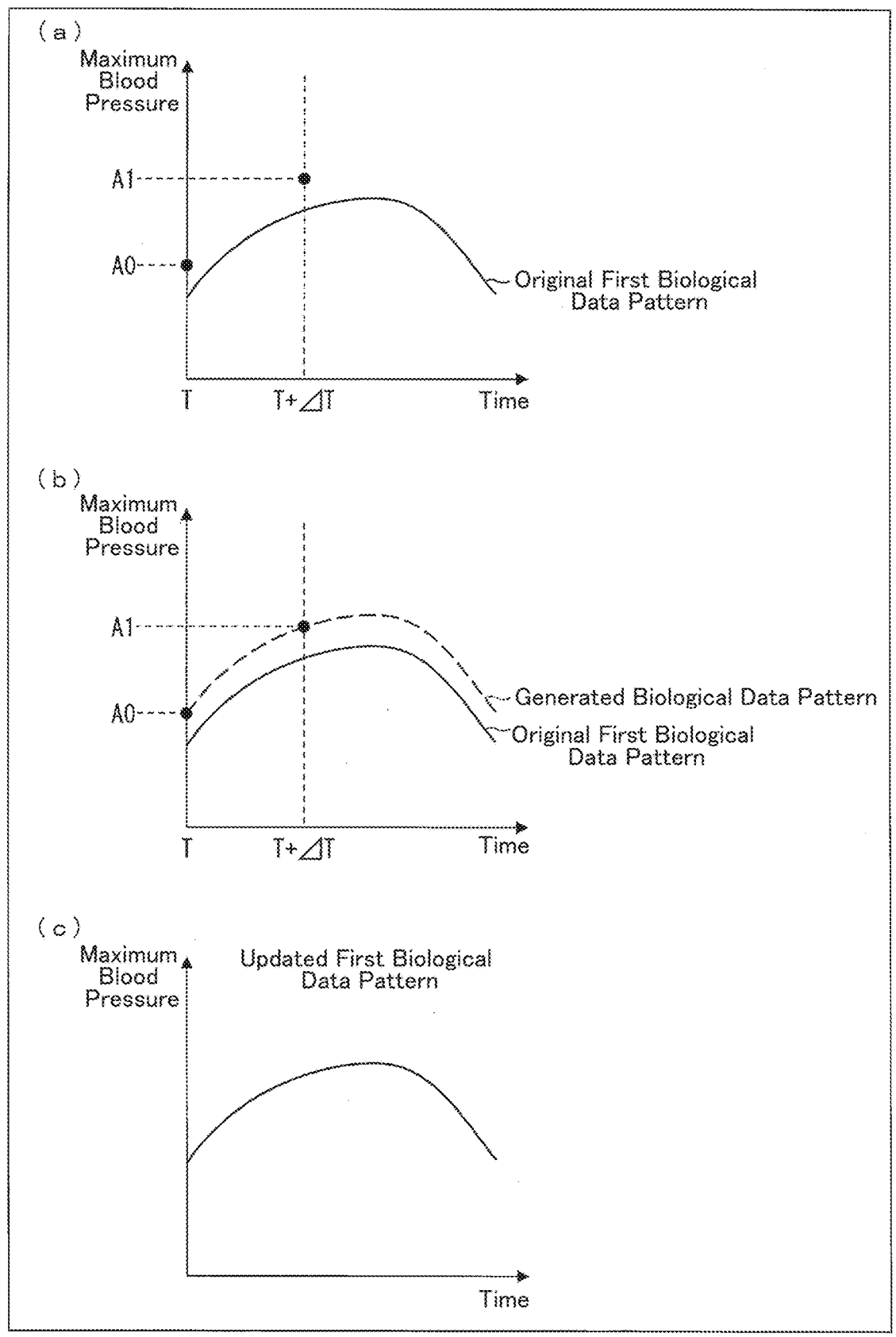

FIG. 8 is a set of diagrams showing an example method of updating a biological data pattern.

Figure 9:
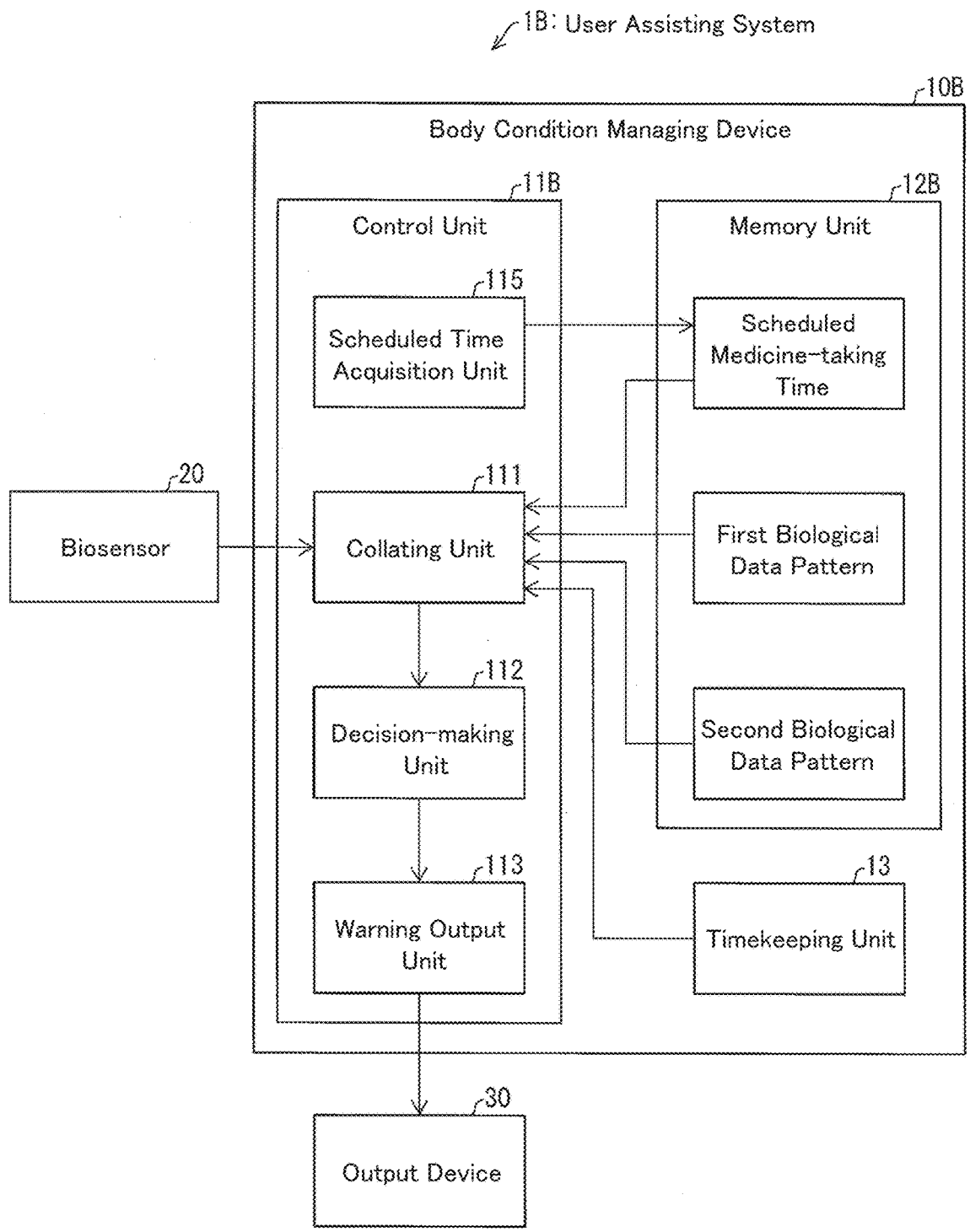

FIG. 9 is a diagram showing an example configuration of a user assisting system in accordance with Embodiment 3.

Figure 10:
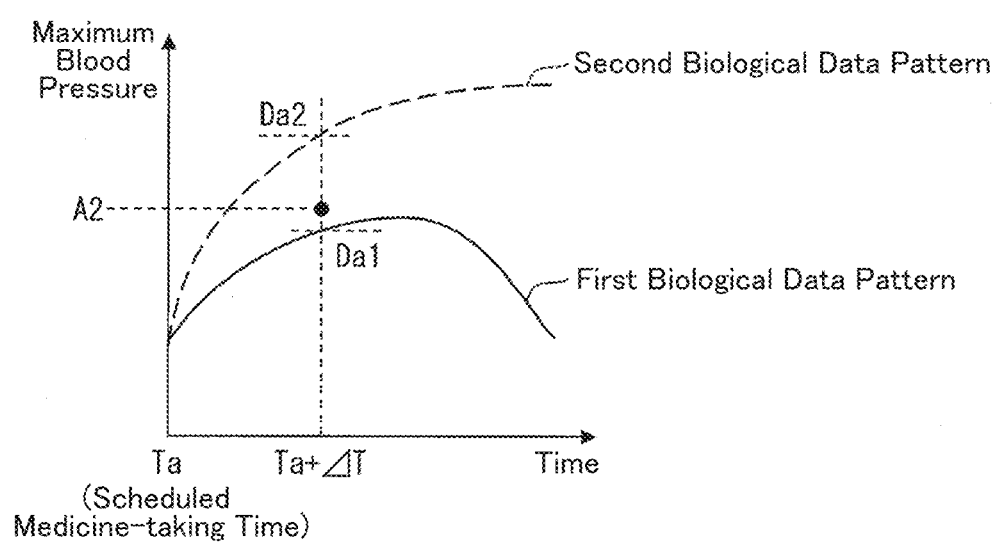

FIG. 10 is a diagram showing an example method of collating biological data and first and second biological data patterns in accordance with Embodiment 3.

Figure 11:
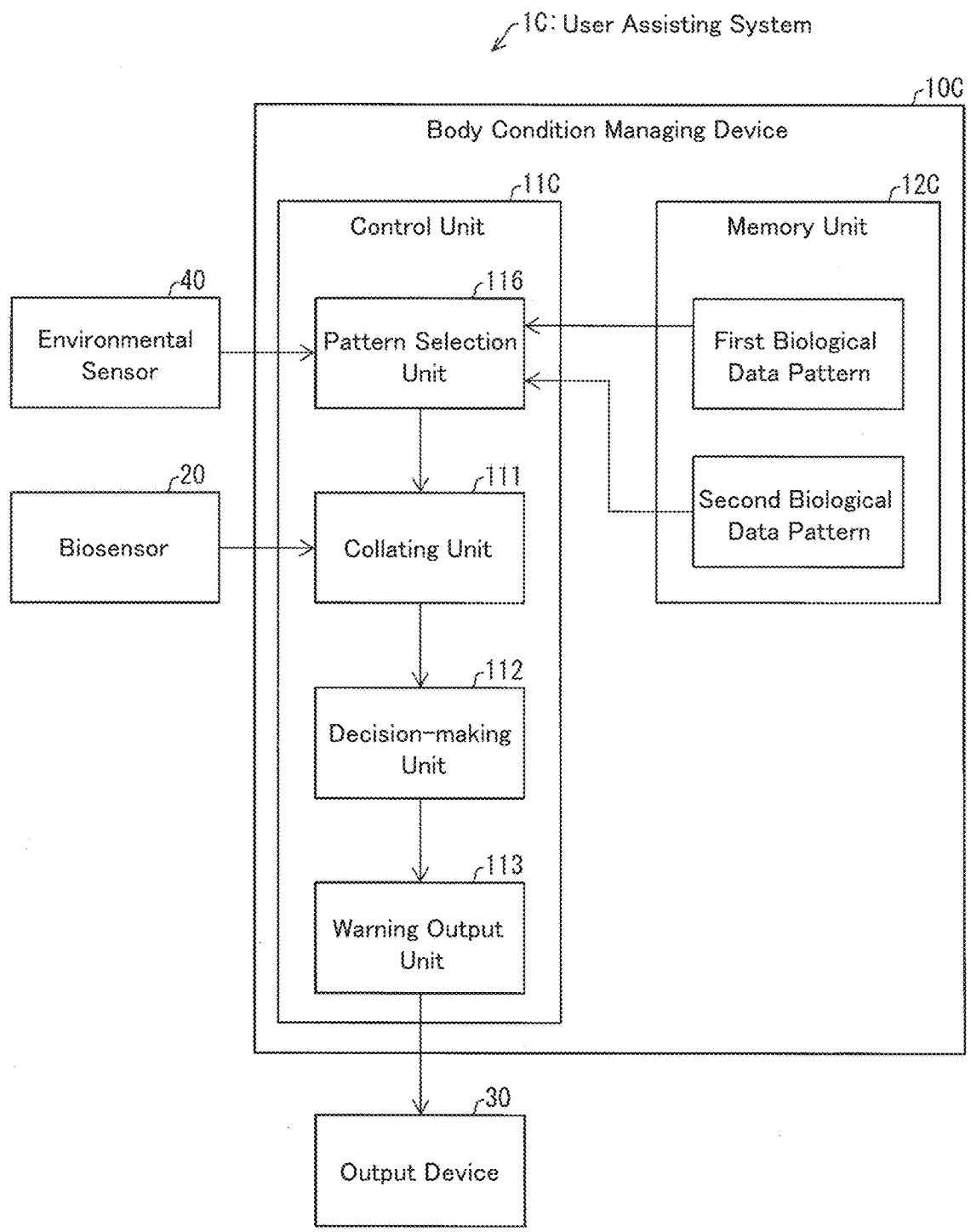

FIG. 11 is a diagram showing an example configuration of a user assisting system in accordance with Embodiment 4.

Figure 12:
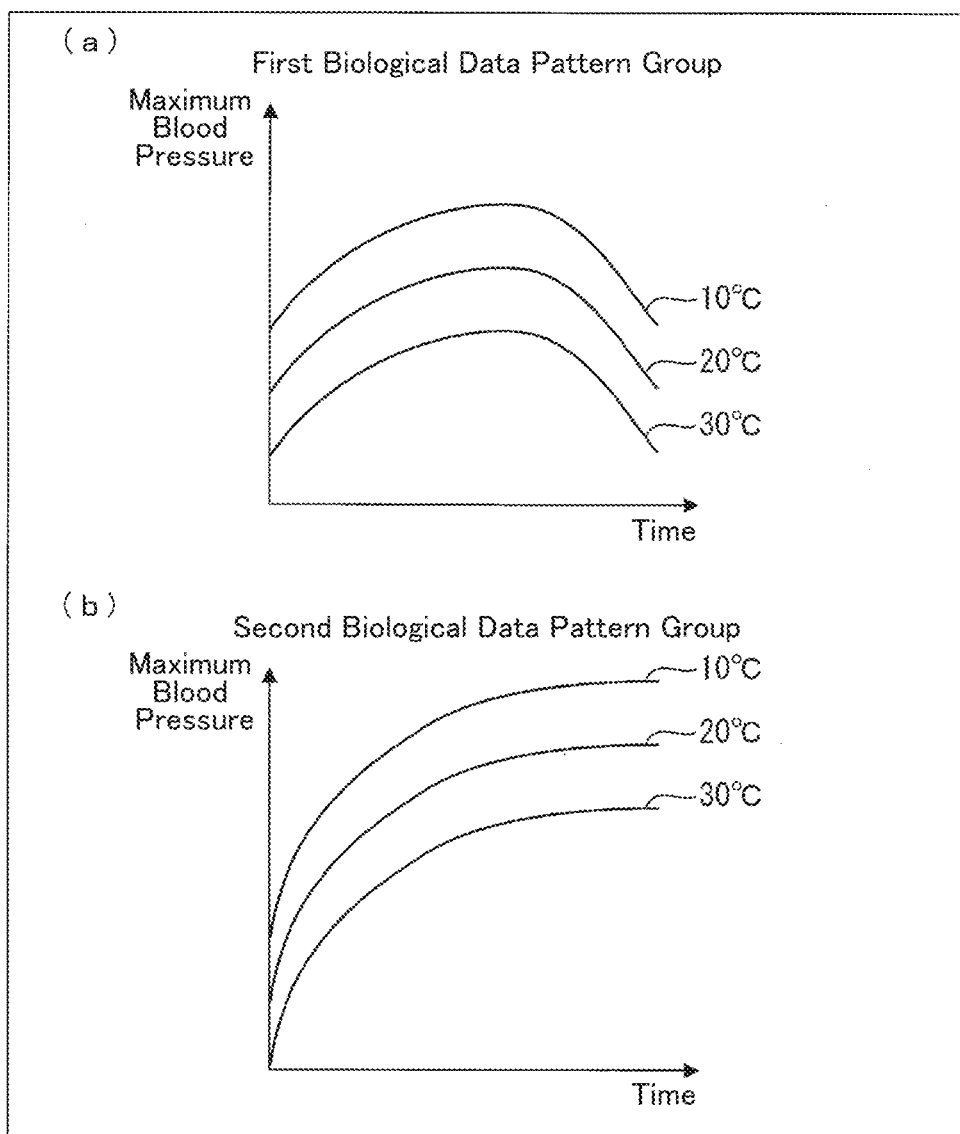

Portion (a) of FIG. 12 is a diagram showing an example first biological data pattern group in accordance with Embodiment 4, and (b) of FIG. 12 is a diagram showing an example second biological data pattern group in accordance with Embodiment 4.

Figure 13:
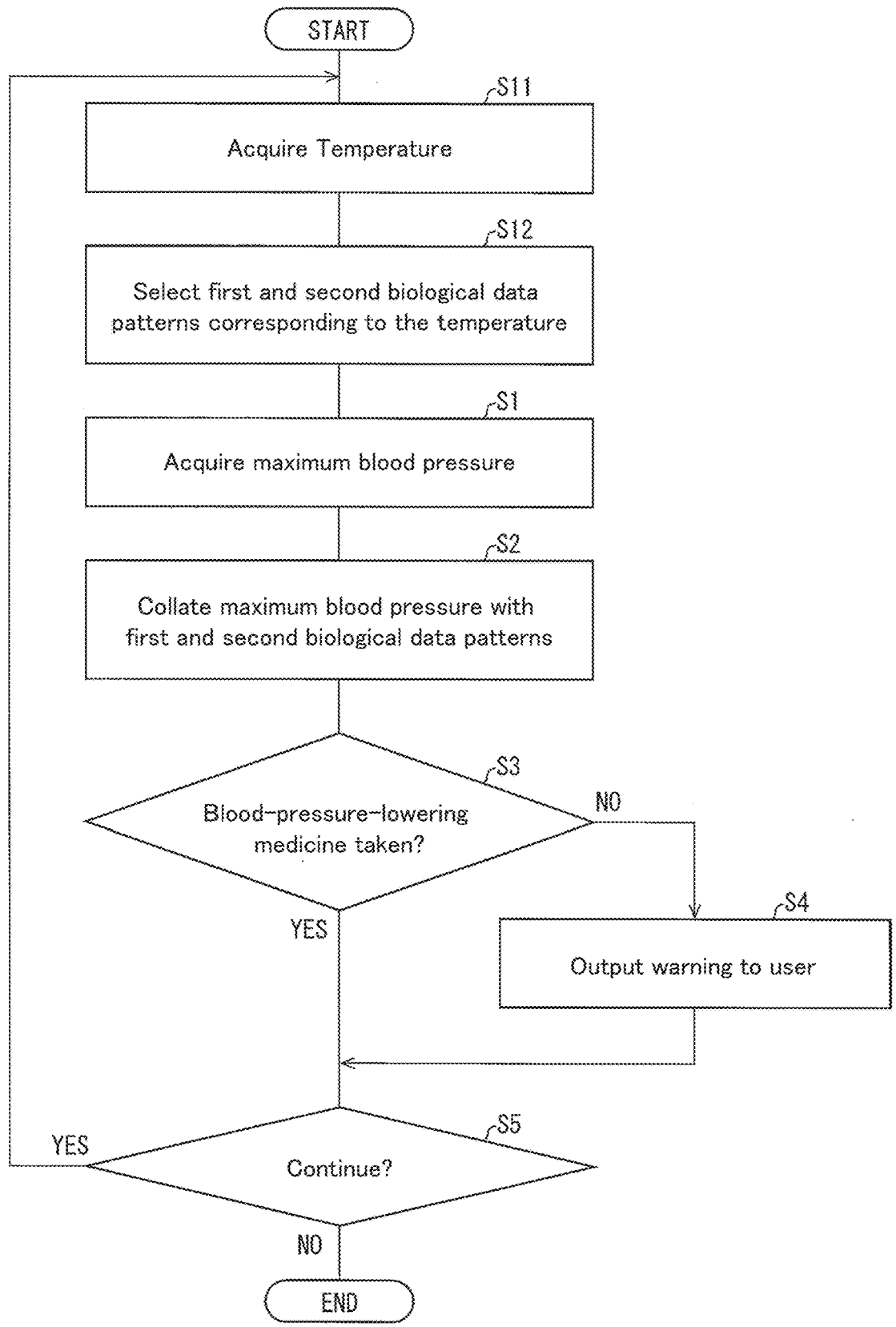

FIG. 13 is a flow chart representing an example medicine-taking managing method in accordance with Embodiment 4.

Figure 14:
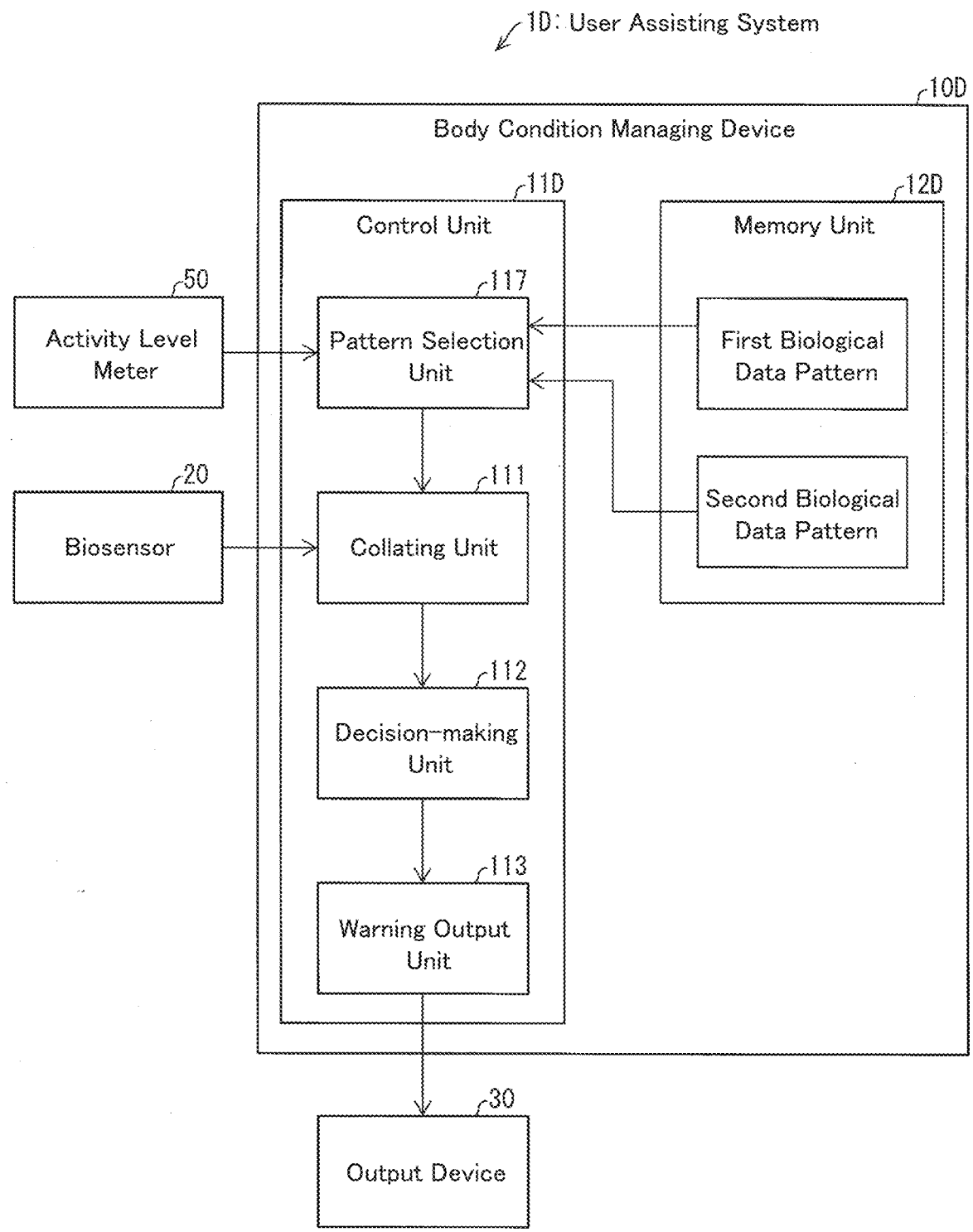

FIG. 14 is a diagram showing an example configuration of a user assisting system in accordance with Embodiment 5.

Figure 15:
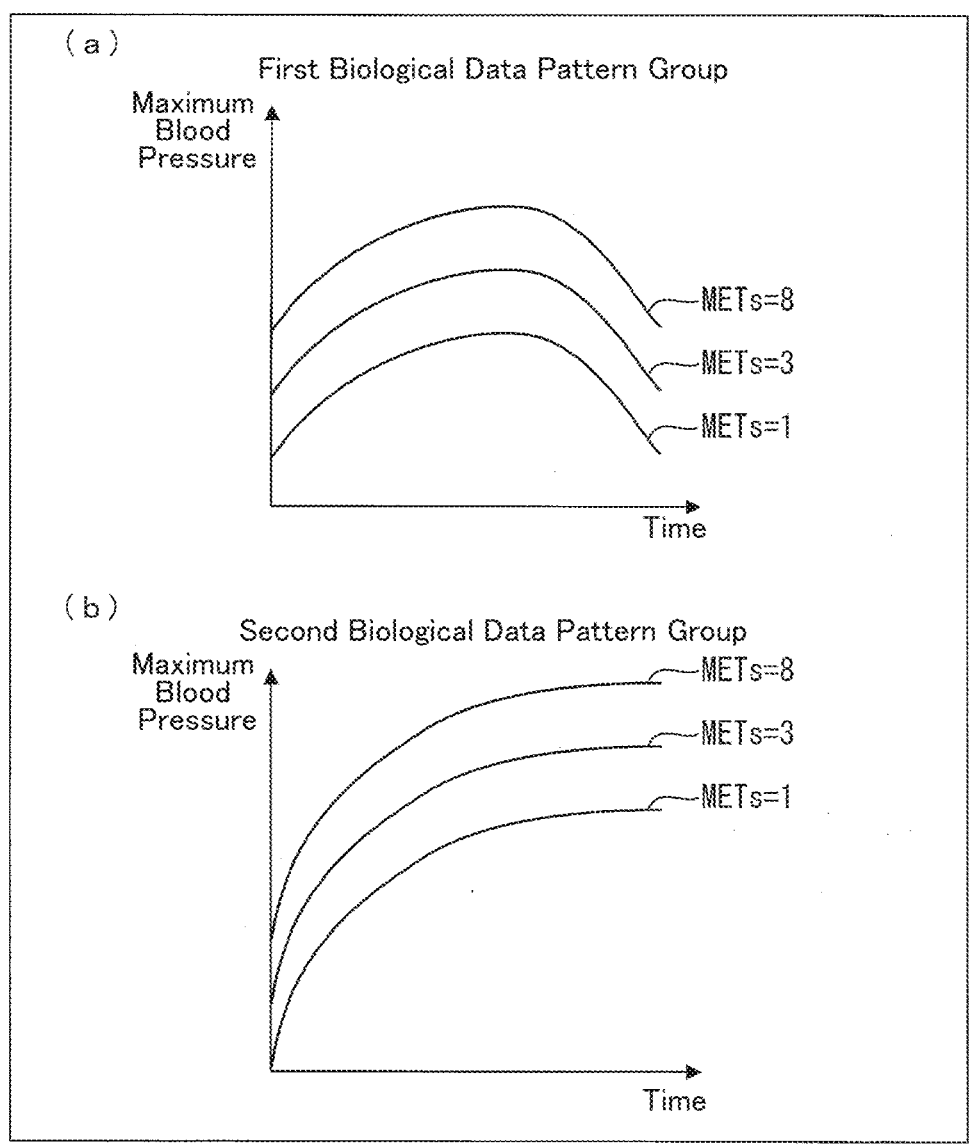

Portion (a) of FIG. 15 is a diagram showing an example first biological data pattern group in accordance with Embodiment 5, and (b) of FIG. 15 is a diagram showing an example second biological data pattern group in accordance with Embodiment 5.

Figure 16:
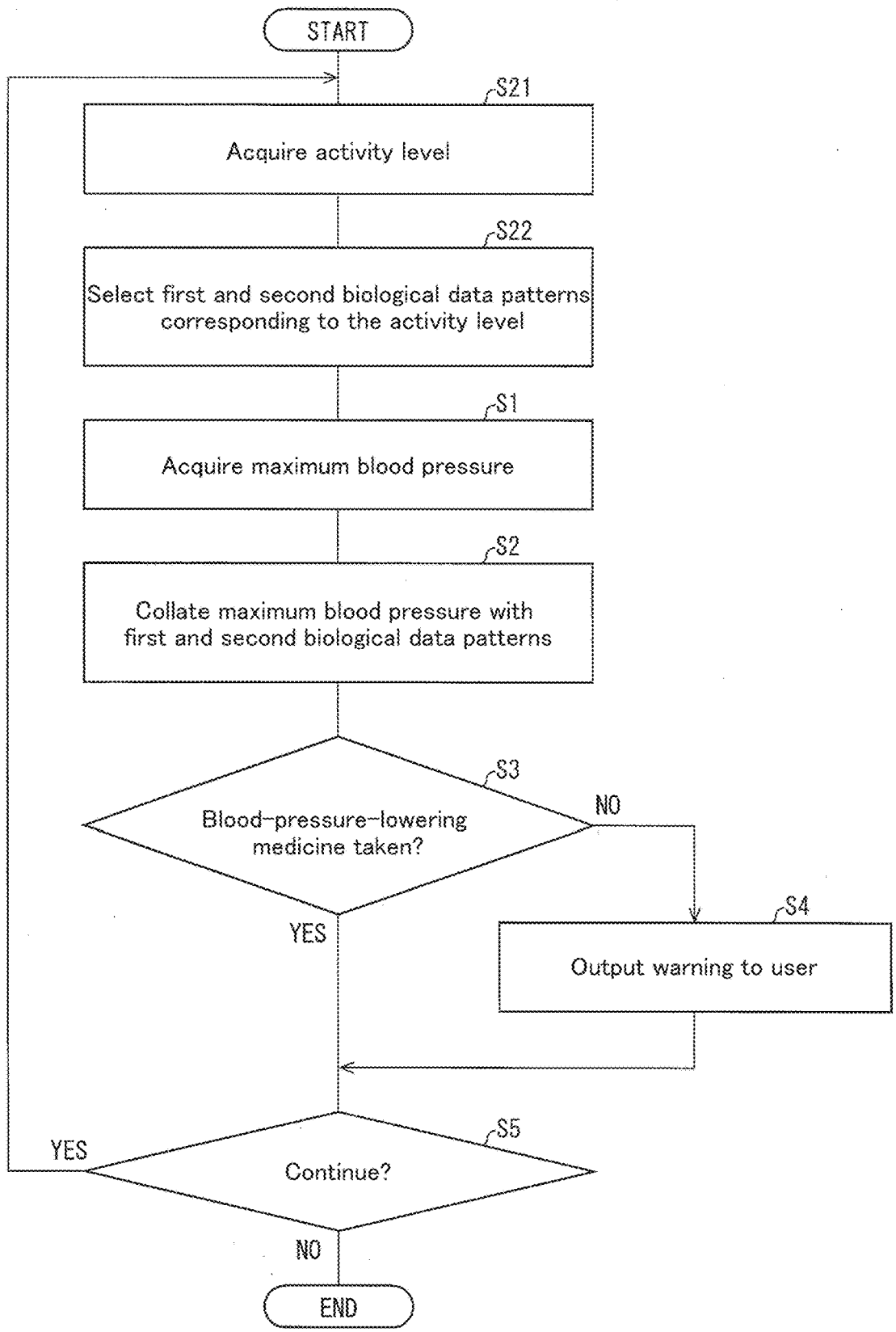

FIG. 16 is a flow chart representing an example medicine-taking managing method in accordance with Embodiment 5.

DESCRIPTION OF EMBODIMENTS

Embodiment 1

An embodiment of the present disclosure will be now described with reference to FIGS. 1 to 6.

User Assisting System

Figure 1:
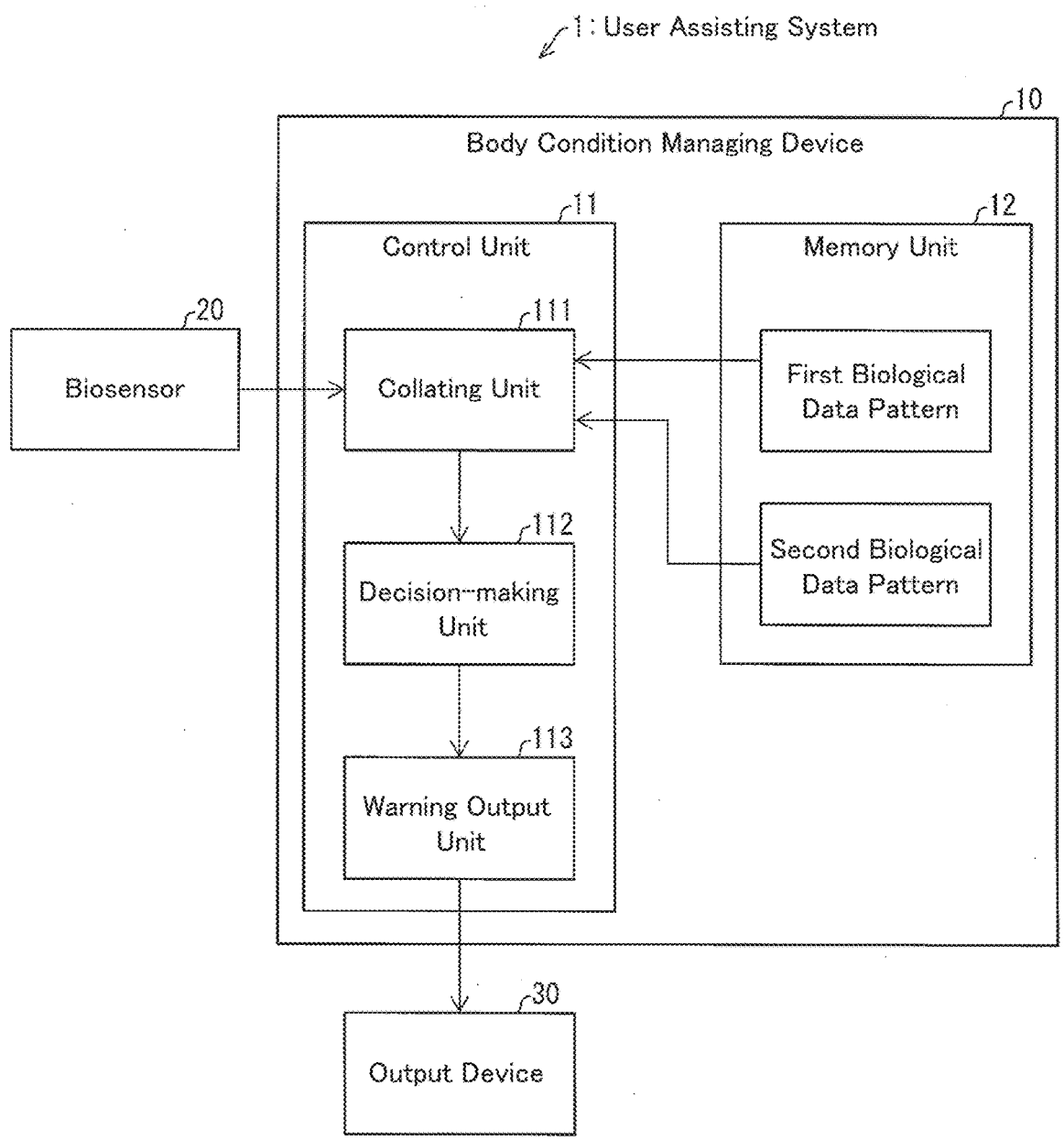
FIG. 1 is a diagram showing an example configuration of a user assisting system in accordance with Embodiment 1.

FIG. 1 is a diagram showing an example configuration of a user assisting system 1 in accordance with the present embodiment. The user assisting system 1 determines whether or not a user (living body) has taken a medicine (ingestible object). Upon determining that the user has not taken the medicine, the user assisting system 1 gives a warning to the user. Referring to FIG. 1, the user assisting system 1 includes a body condition managing device 10, a biosensor 20 (biological data acquisition unit), and an output device 30. The body condition managing device 10 is connected in a communicable manner to the biosensor 20 and the output device 30. The body condition managing device 10 will be described later in more detail.

The biosensor 20 acquires biological data representing the condition of the user. The biosensor 20 acquires data representing, for example, the user's blood pressure, heart rate, body temperature, or skin surface water content as biological data. In other words, the biosensor 20 may be a blood pressure meter for measuring the user's blood pressure, a pulse rate meter for measuring the user's heart rate, a clinical thermometer for taking the user's body temperature, or a perspiration level sensor for measuring the user's skin surface water content.

The biosensor 20 may be, for example, a wearable sensor or a non-contact sensor. The latter type of sensor can acquire biological data, for example, in response to a camera or a microwave sensor detecting that the user has entered a measurement range.

The output device 30 outputs a warning generated by the body condition managing device 10 prompting the user to take a medicine. The output device 30 may output a warning in any manner. The output device 30 may, for example, display a warning image, output a warning sound, or both displays a warning image and outputs a warning sound. The present embodiment illustrates examples where the output device 30 displays a warning image.

The biosensor 20 and the output device 30 may be provided separately from the body condition managing device 10 as in the example shown in FIG. 1. Alternatively, the biosensor 20 and the output device 30 may be built into the body condition managing device 10 unlike the example shown in FIG. 1. As another alternative, the biosensor 20 and the output device 30 may be integrated into a single device.

Configuration of Body Condition Managing Device

Next, a description will be given of the body condition managing device 10 with reference to FIG. 1. The body condition managing device 10 manages the condition of the user, particularly the oral ingestion of a medicine. The body condition managing device 10 includes a control unit 11 and a memory unit 12 as shown in FIG. 1.

The control unit 11 controls the overall operation of the body condition managing device 10 and includes a collating unit 111, a decision-making unit 112, and a warning output unit 113 (output unit). The configuration of the control unit 11 will be specifically described later.

The memory unit 12 contains, for example, various control programs run by the control unit 11 and is built, for example, around a hard disk, a flash memory, or a like non-volatile storage device. The memory unit 12, as an example, contains a first biological data pattern and a second biological data pattern.

Figure 2:
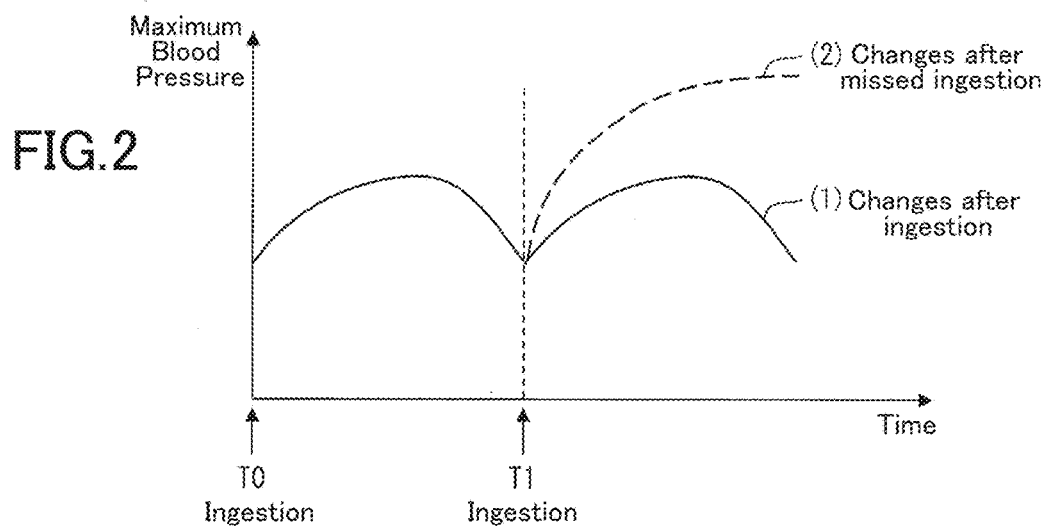
FIG. 2 is a diagram showing example temporal drifting of biological data.

The first and second biological data patterns will be now described with reference to FIGS. 2 and 3. FIG. 2 is a diagram showing example temporal drifting of biological data. Portion (a) of FIG. 3 is a diagram showing an example of the first biological data pattern, and (b) of FIG. 3 is a diagram showing an example of the second biological data pattern.

The following description assumes that the biological data represents a maximum blood pressure. Accordingly, the biosensor 20 is a blood pressure meter, and the user takes a medicine that lowers blood pressure (which will hereinafter be referred to as a "blood-pressure-lowering medicine"), throughout the rest of the description. In examples where the biological data represents something different from a maximum blood pressure, the biosensor 20 and the medicine taken by the user differ accordingly from the specific examples given above. For instance, if the biological data represents body temperature, the biosensor 20 is a thermometer, and the user takes a medicine that regulates body temperature (e.g., antipyretic).

Referring to FIG. 2, the user takes a medicine that lowers blood pressure (which will hereinafter be referred to as a "blood-pressure-lowering medicine") at prescribed times (times T0 and T1 in FIG. 2). If the user takes the blood-pressure-lowering medicine at a prescribed time, the user's maximum blood pressure falls after gently rising as shown in FIG. 2. On the other hand, if the user fails to take the blood-pressure-lowering medicine at a prescribed time, the user's maximum blood pressure quickly rises without falling, as shown in FIG. 2.

These exemplary cases demonstrate that the maximum blood pressure follows different temporal drifting patterns, depending on whether or not the user has taken the blood-pressure-lowering medicine. It can be determined whether or not the user has taken the blood-pressure-lowering medicine, by collating these patterns and the maximum blood pressure. The body condition managing device 10 accordingly stores, in the memory unit 12, the first biological data pattern of the temporal drifting of the maximum blood pressure of the user having taken the blood-pressure-lowering medicine and the second biological data pattern of the temporal drifting of the maximum blood pressure of the user having failed to take the blood-pressure-lowering medicine at an appropriate time. The first and second biological data patterns will be collectively referred to as the "biological data patterns" throughout the rest of the description unless the first and second biological data patterns need to be distinguished.

The biological data patterns do not need to be contained in the memory unit 12 in advance and simply have to be prepared before the collating unit 111 collates the biological data and the biological data patterns. If the biological data patterns are not contained in the memory unit 12 in advance, the biological data patterns, for example, may be inputted upon the collation from an input unit (not shown) on which the user can make manual inputs. The collation will be described later in more detail.

Configuration of Control Unit

The collating unit 111 collates the biological data acquired by the biosensor 20 with the first and second biological data patterns contained in the memory unit 12. A detailed description will be now given of the collation performed by the collating unit 111 with reference to FIG. 4. FIG. 4 is a diagram showing a collation method implemented by the collating unit 111 in accordance with the present embodiment.

The collating unit 111 controls the biosensor 20 to acquire a maximum blood pressure around the time when the user takes a blood-pressure-lowering medicine. Specifically, the collating unit 111 controls the biosensor 20 to acquire a maximum blood pressure and transmit the acquired maximum blood pressure to the collating unit 111, by sending a request to acquire a maximum blood pressure to the biosensor 20. A maximum blood pressure may be acquired in this manner, for example, at a timing determined from the first biological data pattern and a time when the user took the blood-pressure-lowering medicine for the first time. In other words, the control unit 11 may determine a medicine-taking interval at which the blood-pressure-lowering medicine is to be taken on the basis of the first biological data pattern so that a maximum blood pressure can be acquired when the determined medicine-taking interval has elapsed since the user took the blood-pressure-lowering medicine for the first time. After that, a maximum blood pressure is acquired every time the determined medicine-taking interval has elapsed.

The biosensor 20 may acquire and store a maximum blood pressure irrespective of the acquisition request. When this is actually the case, the biosensor 20, upon receiving an acquisition request, transmits to the collating unit 111 the latest maximum blood pressure acquired before the reception of the acquisition request. This example describes the timings at which a maximum blood pressure is to be acquired as being managed by the collating unit 111. Alternatively, the timings may be managed by the biosensor 20.

The collating unit 111 collates the acquired maximum blood pressure with the first and second biological data patterns to identify, on the first and second biological data patterns, the points that correspond to the acquired maximum blood pressure. In the example of FIG. 4, the collating unit 111 determines that maximum blood pressure A0 acquired at time T corresponds to the points on the first and second biological data patterns where the patterns intersect the vertical axis (i.e., the maximum blood pressure at time=0, or when zero time has elapsed since the time when the blood-pressure-lowering medicine should be taken).

After acquiring a maximum blood pressure around the time when the user takes the blood-pressure-lowering medicine, the collating unit 111 acquires a maximum blood pressure once again when a prescribed time has elapsed since that time. The collating unit 111, in the example of FIG. 4, acquires maximum blood pressure A0 at time T and thereafter acquires maximum blood pressure A1 at time T+ΔT. The collating unit 111 then collates maximum blood pressure A1 with maximum blood pressures D1 and D2 on the first and second biological data patterns for time T+ΔT to deduce whether maximum blood pressure A1 is closer to maximum blood pressure D1 or closer to maximum blood pressure D2. For instance, the collating unit 111 deduces which of maximum blood pressures D1 and D2 differs from maximum blood pressure A1 by a quantity that is less than or equal to prescribed value.

In other words, the collating unit 111 deduces whether the user's maximum blood pressure shows temporal drifting that is closer to the first biological data pattern or closer to the second biological data pattern. The collating unit 111 then outputs a deduced result to the decision-making unit 112. Because maximum blood pressure A1 is closer to maximum blood pressure D2 in the example of FIG. 4, the collating unit 111 outputs to the decision-making unit 112 a deduced result that the user's maximum blood pressure shows temporal drifting that is closer to the second biological data pattern.

The collating unit 111 may be in some cases unable to deduce whether maximum blood pressure A1 is closer to maximum blood pressure D1 or closer to maximum blood pressure D2. That can happen, for example, when maximum blood pressures D1 and D2 each differ from maximum blood pressure A1 by a quantity that is greater than a prescribed value. In these cases, the collating unit 111 acquires maximum blood pressure A2 for time T+2ΔT from the biosensor 20 and deduces whether maximum blood pressure A1 is closer to maximum blood pressure D1 or closer to maximum blood pressure D2.

The collating unit 111 does not necessarily collate maximum blood pressure A1 with maximum blood pressures D1 and D2 as described in the example above. For instance, the collating unit 111 may acquire a maximum blood pressure from the biosensor 20 not necessarily around the time when the user takes the blood-pressure-lowering medicine, but at any timing. In this example, the collating unit 111 identifies a point on the first and second biological data patterns that is the closest to the acquired maximum blood pressure and then notifies the decision-making unit 112 whether the identified point is on the first biological data pattern or on the second biological data pattern. If the collating unit 111 fails to identify a single point that is the closest to the acquired maximum blood pressure, the collating unit 111 acquires a maximum blood pressure from the biosensor 20 and performs the same process again when a prescribed time has elapsed. In other words, if so, the collating unit 111 acquires a maximum blood pressure from the biosensor 20 and performs the same process every time a prescribed time has elapsed, until the collating unit 111 identifies a single point that is the closest to the acquired maximum blood pressure.

The decision-making unit 112 determines whether or not the user has taken a blood-pressure-lowering medicine. Specifically, the decision-making unit 112 determines that the user has taken a blood-pressure-lowering medicine if the decision-making unit 112 acquires a result of identification from the collating unit 111 that the user's maximum blood pressure shows temporal drifting that is closer to the first biological data pattern. On the other hand, if the decision-making unit 112 acquires a result of identification from the collating unit 111 that the user's maximum blood pressure shows temporal drifting that is closer to the second biological data pattern, the decision-making unit 112 determines that the user has failed to take a blood-pressure-lowering medicine. The decision-making unit 112, upon determining that the user has failed to take a blood-pressure-lowering medicine, instructs the warning output unit 113 to output a warning prompting the user to take a blood-pressure-lowering medicine.

In response to the instruction from the decision-making unit 112, the warning output unit 113 transmits a warning image prompting the user to take a blood-pressure-lowering medicine to the output device 30 for display of the warning image. If the output device 30 outputs an audible warning, the warning output unit 113 transmits a warning sound prompting the user to take a blood-pressure-lowering medicine to the output device 30. The warning image and sound may be stored as such in the memory unit 12. Alternatively, data from which the warning image or sound can be generated may be stored in the memory unit 12, in which case the warning output unit 113 retrieves the data and generates a warning image or sound.

The warning image and sound may be stored in the output device 30 and may be generated by the output device 30. In the current example, the decision-making unit 112 instructs the output device 30 to output a warning, which means that the warning output unit 113 may be omitted in the current example.

FIG. 5 is an illustration of example warning images being displayed. For instance, if it is determined that the user has failed to take a blood-pressure-lowering medicine, the warning output unit 113 may cause the output device 30 to display a warning image with the content shown in (a) of FIG. 5. The warning output unit 113 may output different types of warning images depending on whether or not the maximum blood pressure acquired by the biosensor 20 exceeds a prescribed threshold. For instance, when the maximum blood pressure acquired by the biosensor 20 does not exceed a prescribed threshold, the warning output unit 113 causes the output device 30 to display a warning image with a non-urgent content shown in (a) of FIG. 5. On the other hand, when the maximum blood pressure acquired by the biosensor 20 exceeds a prescribed threshold, the warning output unit 113 causes the output device 30 to display a warning image with an urgent content as shown in (b) of FIG. 5.

Whether or not an acquired maximum blood pressure exceeds a prescribed threshold may be determined by the control unit 11 (e.g., any of the collating unit 111, the decision-making unit 112, and the warning output unit 113) retrieving a threshold from (not shown) the memory unit 12 and comparing the maximum blood pressure acquired by the biosensor 20 with the threshold. The example above involves one threshold and may alternatively involve a plurality of thresholds. In the current example, the output device 30 displays a warning image with an increasingly more urgent content every time the acquired maximum blood pressure exceeds a new threshold.

If the acquired maximum blood pressure exceeds a prescribed threshold, the warning output unit 113 may notify the user's preregistered family member and/or hospital via a communications unit (not shown) that the user is having a dangerous symptom. For instance, the warning output unit 113 may send an email containing a message that the user is having a dangerous symptom to the email address of the user's family member or attending doctor. The warning output unit 113 may send such an email message in place of, or in addition to, a warning output from the output device 30.

Medicine-Taking Managing Method

Next will be described a method of managing the ingestion of medicines based on biological data with reference to FIG. 6. FIG. 6 is a flow chart representing an example medicine-taking managing method (body condition managing method) in accordance with the present embodiment.

Referring to FIG. 6, the collating unit 111 acquires a maximum blood pressure from the biosensor 20 at a suitable timing (step S1, or the biological data acquisition step; in the rest of the description, the identifier, "step," is omitted before numbered steps). The collating unit 111 retrieves the first and second biological data patterns from the memory unit 12 and collates the retrieved first and second biological data patterns with an acquired maximum blood pressure (S2, or the collating step). The collating unit 111 then outputs to the decision-making unit 112 a result of the collation indicating whether the user's maximum blood pressure shows temporal drifting that is closer to the first biological data pattern or closer to the second biological data pattern.

The decision-making unit 112 determines, from the result of the collation, whether or not the user has taken a blood-pressure-lowering medicine (S3). Specifically, if the user's maximum blood pressure shows temporal drifting that is closer to the first biological data pattern, the decision-making unit 112 determines that the user has taken a blood-pressure-lowering medicine. On the other hand, if the user's maximum blood pressure shows temporal drifting that is closer to the second biological data pattern, the decision-making unit 112 determines that the user has failed to take a blood-pressure-lowering medicine.

Upon determining that the user has failed to take a blood-pressure-lowering medicine (NO in S3), the decision-making unit 112 outputs to the warning output unit 113 an instruction for an output of a warning. The warning output unit 113 causes the output device 30 to output a warning to the user in response to the instruction (S4, or the output step). Thereafter, if settings have been made to repeat S1 to S4 (YES in S5), the control unit 11 returns the medicine-taking managing process to S1. On the other hand, if settings have not been made to repeat S1 to S4 (NO in S5), the control unit 11 ends the process.

Upon determining that the user has taken a blood-pressure-lowering medicine (YES in S3), the decision-making unit 112 outputs no instructions to the warning output unit 113. The process thus skips S4 and proceeds to S5.

Main Effects

The body condition managing device 10 is capable of determining whether or not the user has taken a medicine, by collating the biological data acquired by the biosensor 20 with the first and second biological data patterns. In other words, if the user has failed to take a medicine at a timing when the medicine should be taken, the body condition managing device 10 can identify the situation. Hence, the body condition managing device 10 can determine whether or not the user has taken a medicine without having to receive an input of, for example, medicine-taking records from the user of the body condition managing device 10 even when the user is taking medicines manually.

Since the body condition managing device 10 is capable of determining that the user has failed to take a medicine, the body condition managing device 10 can perform a suitable process to urge the user to take a medicine. For instance, the body condition managing device 10 can output a warning prompting the user to take a medicine. The body condition managing device 10 hence prevents the user from forgetting to take a medicine.

Variation Examples

The following variation examples are applicable to the present embodiment and equally to the embodiments detailed later in the description.

The body condition managing device 10 does not necessarily determine only whether or not the user has taken a medicine, but may also determine whether or not the user has taken food for health improvement or symptom alleviation (including nutritional supplements). In other words, the body condition managing device 10 may determine whether or not the user has taken any predetermined ingestible object intended to be taken into a living body. Additionally, the body condition managing device 10 does not necessarily determine only whether or not the user has taken (i.e., orally ingested) a medicine, but may also determine whether or not the user has non-orally ingested a medicine, for example, by way of percutaneous absorption or injection.

Embodiment 1 has so far described examples where the user is the person who takes the medicine. Alternatively, the user may not be the living body that takes the medicine. Specifically, the living body may be a family member of the user. If the user is a doctor or nurse, the living body may be a patient. The living body is not necessarily a human. For instance, the living body that takes the medicine may be an animal bred by the user.

Embodiment 1 has so far described examples where the first and second biological data patterns are both contained in the memory unit 12 in the form of graphs representing a relationship between time and biological data (maximum blood pressure in the examples given in Embodiment 1). The biological data patterns are however not necessarily given in the form of graphs. For instance, the biological data patterns may be given in the form of tables that associate time and biological data and may be given in the form of approximation formulae and parameters. In addition, the biological data pattern may represent discrete biological data (e.g., the biological data pattern may show data points with a few minutes' intervals). Furthermore, the biological data pattern may give biological data in the form of changes over time from an initial value.

Embodiment 1 has so far described examples where the body condition managing device 10 outputs information (warning images in the examples given in Embodiment 1) only when the user has been determined not to have taken the medicine. The body condition managing device 10 may alternatively output information also when the user has been determined to have taken the medicine. For instance, the body condition managing device 10 may output via the output device 30 an image or sound indicating that the body condition managing device 10 has confirmed that the user has taken the medicine. The body condition managing device 10 may send an email containing a message that the body condition managing device 10 has confirmed that the user has taken the medicine, to a family member or an attending doctor via a communications unit (not shown).

Embodiment 2

Another embodiment of the present disclosure will be described next with reference to FIGS. 7 and 8. For convenience of description, members of the present embodiment that have the same function as members of the previous embodiment are indicated by the same reference numerals, and description thereof is omitted.

The present embodiment illustrates a user assisting system 1A and a body condition managing device 10A that are capable of updating biological data patterns on the basis of the biological data acquired from the biosensor 20.

Configuration of Body Condition Managing Device

FIG. 7 is a diagram showing an example configuration of the user assisting system 1A in accordance with the present embodiment. The user assisting system 1A differs from the user assisting system 1 of Embodiment 1 in that the former includes the body condition managing device 10A.

The body condition managing device 10A differs from the body condition managing device 10 of Embodiment 1 in that the former includes a control unit 11A. The control unit 11A differs from the control unit 11 of Embodiment 1 in that the former additionally includes an update unit 114.

The update unit 114 updates the biological data patterns contained in the memory unit 12 on the basis of the biological data acquired from the biosensor 20. A description will be now given of a method of updating a biological data pattern with reference to FIG. 8. FIG. 8 is a set of diagrams showing an example method of updating a biological data pattern. The following description, taking the first biological data pattern as an example, is equally applicable to the second biological data pattern.

Assume that the collating unit 111 has acquired maximum blood pressures A0 and A1 shown in (a) of FIG. 8 from the biosensor 20. Maximum blood pressures A0 and A1 are located close to the first biological data pattern, but indicate slightly higher values than the first biological data pattern as shown in FIG. 8. The collating unit 111 outputs maximum blood pressures A0 and A1 to the update unit 114.

The update unit 114 generates a biological data pattern on the basis of the maximum blood pressures acquired from the collating unit 111. Specifically, the update unit 114 generates a data pattern passing through maximum blood pressures A0 and A1 that gently rises before falling similarly to the temporal drifting of the first biological data pattern (see (b) of FIG. 8). The update unit 114 then replaces the first biological data pattern contained in the memory unit 12 with this generated data pattern. The first biological data pattern contained in the memory unit 12 is thus altered to have higher values than the original first biological data pattern (see (c) of FIG. 8).

The biological data pattern is not necessarily updated by the example method shown in FIG. 8. For instance, the update unit 114 may replace the original biological data pattern with the raw biological data acquired during a prescribed period (specifically, a period that corresponds to the range of time for the biological data pattern) starting around the time when the user takes a blood-pressure-lowering medicine. As an alternative example, the update unit 114 may update the biological data pattern through prescribed computation (e.g., averaging).

Main Effects

The body condition managing device 10A, as described so far, is capable of updating the biological data pattern contained in the memory unit 12 on the basis of the biological data acquired from the biosensor 20. In other words, the body condition managing device 10A is hence capable of providing at all times a biological data pattern that is suitable for the condition of the user.

The update unit 114 updates the second biological data pattern if the biological data acquired from the biosensor 20 is close to the second biological data pattern.

Embodiment 2 has so far described examples where the update unit 114 updates a biological data pattern on the basis of the biological data acquired from the biosensor 20. The update unit 114 does not necessarily update the biological data pattern as described in those examples. For instance, the update unit 114 may receive a biological data pattern that matches the user's attributes from a server (not shown) managing a plurality of biological data patterns prepared based on the living body's attributes via a communications unit (not shown), in order to update that biological data pattern. Examples of attributes include age, body height, body weight, and gender.

For instance, the update unit 114 may communicate with the server on the user's birthday to receive a biological data pattern that matches the user's age. The user may input his/her age and birthday in advance via an input unit (not shown) to have them stored in the memory unit 12.

Embodiment 3

Another embodiment of the present disclosure will be described next with reference to FIGS. 9 and 10. For convenience of description, members of the present embodiment that have the same function as members of a previous embodiment are indicated by the same reference numerals, and description thereof is omitted.

The present embodiment illustrates a user assisting system 1B and a body condition managing device 10B that are capable of determining a timing for acquiring biological data on the basis of a predetermined scheduled medicine-taking time (scheduled time).

Configuration of Body Condition Managing Device

FIG. 9 is a diagram showing an example configuration of the user assisting system 1B in accordance with the present embodiment. The user assisting system 1B differs from the user assisting system 1 of Embodiment 1 in that the former includes the body condition managing device 10B.

The body condition managing device 10B differs from the body condition managing device 10 of Embodiment 1 in that the former includes a control unit 11B, a memory unit 12B, and a timekeeping unit 13. The control unit 11B differs from the control unit 11 of Embodiment 1 in that the former additionally includes a scheduled time acquisition unit 115 (time acquisition unit). The memory unit 12B differs from the memory unit 12 of Embodiment 1 in that the former additionally contains a scheduled medicine-taking time. The timekeeping unit 13 is a so-called "clock" that keeps the current time.

The scheduled time acquisition unit 115 acquires a scheduled medicine-taking time that is time information representing the time when the user should take the medicine. The scheduled time acquisition unit 115 acquires as the scheduled medicine-taking time, for example, the time inputted on an input unit (not shown) by the user. The scheduled time acquisition unit 115 stores the acquired scheduled medicine-taking time in the memory unit 12B. The scheduled time acquisition unit 115 does not necessarily acquire a scheduled medicine-taking time by this example method. For instance, the scheduled time acquisition unit 115 may acquire via a communications unit (not shown) the time inputted by the user on a terminal device communicable with the body condition managing device 10B. There may be a plurality of scheduled medicine-taking times.

A description will be now given of a collation method in accordance with the present embodiment with reference to FIG. 10. FIG. 10 is a diagram showing a collation method implemented by the collating unit 111 in accordance with the present embodiment.

The collating unit 111 acquires the current time from the timekeeping unit 13 and retrieves a scheduled medicine-taking time from the memory unit 12B. If the current time matches the scheduled medicine-taking time, the collating unit 111 controls the biosensor 20 after a prescribed period of time to acquire a maximum blood pressure.

Specifically, as shown in FIG. 10, the collating unit 111 acquires a maximum blood pressure from the biosensor 20 upon time $\Delta T$ having passed since scheduled medicine-taking time Ta. The collating unit 111 then collates acquired maximum blood pressure A2 with maximum blood pressures Da1 and Da2 for time Ta+$\Delta T$ to deduce whether maximum blood pressure A2 is closer to maximum blood pressure Da1 or closer to maximum blood pressure Da2. Time $\Delta T$ is set to such a value that the first and second biological data patterns develop a significant difference therebetween at time Ta+$\Delta T$.

Referring to FIG. 10, scheduled medicine-taking time Ta is a time at which the biological data patterns intersect the vertical axis. The collating unit 111 therefore can deduce maximum blood pressures Da1 and Da2 on the biological data patterns for time Ta+$\Delta T$ at which the collating unit 111 acquires maximum blood pressure A2 from the biosensor 20. In other words, the collating unit 111 is still capable of deducing whether the temporal drifting of the user's maximum blood pressure is closer to the first biological data pattern or closer to the second biological data pattern by acquiring a maximum blood pressure at least once from the biosensor 20.

Main Effects

The body condition managing device 10C, as described so far, is capable of determining whether or not the user has taken the medicine, based on a small quantity of biological data.

Embodiment 4

Another embodiment of the present disclosure will be described next with reference to FIGS. 11 to 13. For convenience of description, members of the present embodiment that have the same function as members of a previous embodiment are indicated by the same reference numerals, and description thereof is omitted.

The present embodiment illustrates a user assisting system 1C and a body condition managing device 10C that are capable of determining whether or not the user has taken a medicine on the basis of those biological data patterns which match the user's surrounding environment.

Configuration of Body Condition Managing Device

FIG. 11 is a diagram showing an example configuration of the user assisting system 1C in accordance with the present embodiment. The user assisting system 1C differs from the user assisting system 1 of Embodiment 1 in that the former includes the body condition managing device 10C and an environmental sensor 40 (environmental data acquisition unit).

The environmental sensor 40 is connected in a communicable manner to the body condition managing device 10C. The environmental sensor 40 acquires environmental data representing the user's surrounding environment and transmits the acquired environmental data to the body condition managing device 10C. The environmental sensor 40 acquires, for example, data representing either or both of temperature and humidity in the user's surroundings as environmental data. Accordingly, the environmental sensor 40 may be either one or both of a temperature sensor or a humidity sensor. The present embodiment assumes that the environmental sensor 40 is a temperature sensor.

The body condition managing device 10C may be connected not to the environmental sensor 40, but to a receiver (not shown) capable of acquiring environmental data. In such cases, the receiver acquires environmental data from an external device (not shown) containing environmental data. The environmental data may be, for example, information on weather in the user's environment (geographical area). The receiver acquires environmental data from an external device over network lines. The environmental sensor 40 may be integrated with either one or both of the body condition managing device 10C and the biosensor 20.

The body condition managing device 10C differs the body condition managing device 10 of Embodiment 1 in that the former includes a control unit 11C and a memory unit 12C. The control unit 11C differs from the control unit 11 of Embodiment 1 in that the former additionally includes a pattern selection unit 116 (first selection unit). The memory unit 12C differs from the memory unit 12 of Embodiment 1 in that the former contains a first biological data pattern group and a second biological data pattern group.

A description will be now given of the first biological data pattern group and the second biological data pattern group in accordance with the present embodiment with reference to FIG. 12. Portion (a) of FIG. 12 is a diagram showing an example of the first biological data pattern group, and (b) of FIG. 12 is a diagram showing an example of the second biological data pattern group.

Referring to (a) of FIG. 12, the first biological data pattern group in accordance with the present embodiment includes a plurality of first biological data patterns each of which is associated with a different temperature. Referring to (b) of FIG. 12, the second biological data pattern group in accordance with the present embodiment includes a plurality of second biological data patterns each of which is associated with a different temperature. The first and second biological data pattern groups will be collectively referred to as the "biological data pattern groups" throughout the rest of the description unless the first and second biological data pattern groups need to be distinguished.

The user's blood pressure or the amount of change in the blood pressure will increase when temperature falls in the user's surroundings. Accordingly, the biological data pattern groups in accordance with the present embodiment give higher maximum blood pressures for lower temperatures for the same period of time elapsed since the time when the user should take the blood-pressure-lowering medicine. FIG. 12 shows biological data patterns for the surrounding temperatures of 10° C., 20° C., and 30° C. as an example biological data pattern group. The biological data pattern groups given in FIG. 12 are mere examples. The numerical values and shapes of the biological data patterns, the number of the biological data patterns, the temperatures associated with the biological data patterns given in FIG. 12 are mere examples, and the biological data pattern groups are not limited in any particular manner. For more accurate determination, it is preferable that the biological data patterns be prepared with smaller temperature intervals in the possible range of temperatures in the user's surroundings, that is, more biological data patterns be provided in that range.

The pattern selection unit 116 controls the environmental sensor 40 to acquire surrounding temperature around the time when the user takes the blood-pressure-lowering medicine. Specifically, the pattern selection unit 116 sends a request to acquire a temperature to the environmental sensor 40 so that the environmental sensor 40 acquires a temperature and sends the acquired temperature to the pattern selection unit 116. The environmental sensor 40 may acquire a temperature at the same time as, immediately before, or immediately after the collating unit 111 acquires a maximum blood pressure.

The pattern selection unit 116 selects a biological data pattern associated with a temperature that matches, or is the closest to, the acquired temperature from the biological data pattern group and retrieves the selected biological data pattern. The pattern selection unit 116 then outputs the retrieved first and second biological data patterns to the collating unit 111, so that the collating unit 111 can collate the biological data patterns corresponding to the temperature in the user's surroundings with the acquired biological data.

Medicine-Taking Managing Method

Next will be described a method of managing the ingestion of medicines based on biological data with reference to FIG. 13. FIG. 13 is a flow chart representing an example medicine-taking managing method in accordance with the present embodiment. S1 to S5 in FIG. 13 are the same as S1 to S5 in Embodiment 1, and description thereof is omitted.

The pattern selection unit 116 acquires a temperature from the environmental sensor 40 at a suitable timing (S11). The pattern selection unit 116 selects a first and a second biological data pattern associated with the acquired temperature respectively from the first and the second biological data pattern group contained in the memory unit 12C and retrieves the selected biological data patterns (S12). The control unit 11C then implements S1 to S5.

S11 and S12 may be implemented either simultaneously with S1 or between S1 and S2.

Main Effects

The body condition managing device 10C is capable of determining whether or not the user has taken the medicine, by taking temperature in the user's surroundings into account. The body condition managing device 10C is thus capable of more precisely determining whether or not the user has taken the medicine.

Embodiment 5

Another embodiment of the present disclosure will be described next with reference to FIGS. 14 to 16. For convenience of description, members of the present embodiment that have the same function as members of a previous embodiment are indicated by the same reference numerals, and description thereof is omitted.

The present embodiment illustrates a user assisting system 1D and a body condition managing device 10D that are capable of determining whether or not the user has taken a medicine on the basis of those biological data patterns which match the user's activity condition.

Configuration of Body Condition Managing Device

FIG. 14 is a diagram showing an example configuration of the user assisting system 1D in accordance with the present embodiment. The user assisting system 1D differs from the user assisting system 1 of Embodiment 1 in that the former includes the body condition managing device 10D and an activity level meter 50 (activity data acquisition unit).

The activity level meter 50 is connected in a communicable manner to the body condition managing device 10D. The activity level meter 50 acquires activity data representing the user's activity condition and transmits the acquired activity data to the body condition managing device 10D. The activity level meter 50 includes a built-in acceleration sensor and calculates, for example, the user's physical activity level or calorie consumption from the acceleration detected by the acceleration sensor that results from the user's motion. The activity level meter 50 in the present embodiment calculates the METs (metabolic equivalents), which is an indicator of the intensity of a physical activity (activity level), as activity data by converting the physical activity level or calorie consumption into METs.

An MET is an indicator of the activity level of a living body. The MET is equal to 1 when the living body is at rest and can be a measure as to how many times energy the living body consumes when active in comparison to the living body at rest. Accordingly, a greater MET indicates a more vigorous motion of the user.

The activity data acquisition unit, which acquires activity data, is not necessarily the activity level meter 50 and may be, for example, a pedometer. When the activity data acquisition unit is a pedometer, for example, a walking speed or a time needed to take one step is calculated on the basis of the acceleration detected by the built-in acceleration sensor in the pedometer. The pedometer then converts the walking speed or the time needed to take one step into an MET to acquire activity data. In other words, the activity data acquisition unit needs only to include a sensor capable of detecting the user's motion (e.g., acceleration sensor) to acquire activity data.

The present embodiment takes the MET as an example of activity data for the purpose of description. This is by no means intended to limit the scope of the invention. The activity data may alternatively be representative of, for example, the user's physical activity level or calorie consumption acquired by the activity level meter 50 or the walking speed or time needed to take one step acquired by the pedometer.

The activity level meter 50 may further include, for example, a built-in pulse rate meter or heart rate meter in addition to the acceleration sensor to acquire its measurements as activity data. If the activity level meter 50 include a built-in pulse rate meter or heart rate meter, the activity level meter 50 may double as a biosensor that acquires the measurements as biological data.

The example of FIG. 14 shows the activity level meter 50 being provided separately from the body condition managing device 10D and the biosensor 20. Alternatively, the activity level meter 50 may be integrated with either one or both of the body condition managing device 10C and the biosensor 20.

The body condition managing device 10D differs from the body condition managing device 10 of Embodiment 1 in that the former includes a control unit 11D and a memory unit 12D. The control unit 11D differs from the control unit 11 of Embodiment 1 in that the former additionally include a pattern selection unit 117 (second selection unit). The memory unit 12D differs from the memory unit 12 of Embodiment 1 in that the former contains the first biological data pattern group and the second biological data pattern group.

A description will be now given of the first and second biological data pattern groups in accordance with the present embodiment with reference to FIG. 15. Portion (a) of FIG. 15 is a diagram showing an example of the first biological data pattern group, and (b) of FIG. 15 is a diagram showing an example of the second biological data pattern group.

Referring to (a) of FIG. 15, the first biological data pattern group in accordance with the present embodiment includes a plurality of first biological data patterns each of which is associated with a different MET. Referring to (b) of FIG. 15, the second biological data pattern group in accordance with the present embodiment includes a plurality of second biological data patterns each of which is associated with a different MET. The first and second biological data pattern groups will be collectively referred to as the "biological data pattern groups" throughout the rest of the description unless the first and second biological data pattern groups need to be distinguished.

The user's blood pressure or the amount of change in the blood pressure will increase when the user's activity level rises. Accordingly, the biological data pattern groups in accordance with the present embodiment give higher maximum blood pressures for higher METs for the same period of time elapsed since the time when the user should take the blood-pressure-lowering medicine. FIG. 15 shows biological data patterns for the METs of 1, 3, and 8 as an example biological data pattern group. The biological data pattern groups given in FIG. 15 are mere examples. The numerical values and shapes of the biological data patterns, the number of biological data patterns, and the MET values associated with the biological data patterns given in FIG. 15, to name a few, are mere examples, and the biological data pattern groups are not limited in any particular manner. For more accurate determination, it is preferable that the biological data patterns be prepared with smaller MET value intervals in the possible range of METs, that is, more biological data patterns be provided in that range.

The pattern selection unit 117 controls the activity level meter 50 to acquire MET values around the time when the user takes the blood-pressure-lowering medicine. Specifically, the pattern selection unit 117 sends a request to acquire an activity level to the activity level meter so that the activity level meter 50 calculates an MET value and sends the calculated MET value to the pattern selection unit 117. The activity level meter 50 may acquire an MET value at the same time as, immediately before, or immediately after the collating unit 111 acquires a maximum blood pressure.

The pattern selection unit 117 selects a biological data pattern associated with a value that matches, or is the closest to, the acquired MET value from the biological data pattern group and retrieves the selected biological data pattern. The pattern selection unit 117 then outputs the retrieved first and second biological data patterns to the collating unit 111, so that the collating unit 111 can collate the biological data patterns corresponding to the user's activity level with the acquired biological data.

The pattern selection unit 117 may calculate METs. In such cases, the data acquired by the activity level meter 50 or the pedometer is transmitted to the pattern selection unit 117.

Medicine-Taking Managing Method

Next will be described a method of managing the ingestion of medicines based on biological data with reference to FIG. 16. FIG. 16 is a flow chart representing an example medicine-taking managing method in accordance with the present embodiment. S1 to S5 in FIG. 16 are the same as S1 to S5 in Embodiment 1, and description thereof is omitted.

The pattern selection unit 117 acquires an activity level (MET value) from the activity level meter 50 at a suitable timing (S21). The pattern selection unit 117 selects a first and a second biological data pattern associated with the acquired MET value respectively from the first and the second biological data pattern group contained in the memory unit 12D and retrieves the selected biological data patterns (S22). The control unit 11D then implements S1 to S5.

S21 and S22 may be implemented either simultaneously with S1 or between S1 and S2.

Main Effects

The body condition managing device 10D is capable of determining whether or not the user has taken the medicine, by taking the user's activity level into account. The body condition managing device 10D is thus capable of more precisely determining whether or not the user has taken the medicine.

Variation Examples

The user assisting system 1C described in Embodiment 4 and the user assisting system 1D described in Embodiment 5 may be combined to provide a user assisting system 1E. Accordingly, the user assisting system 1E includes a body condition managing device 10E that may retrieve suitable biological data from biological data pattern groups on the basis of the environmental data acquired by the environmental sensor 40 and the activity level acquired by the activity level meter 50. The body condition managing device 10E is thus capable of determining whether or not the user has taken the medicine, by taking the user's surrounding environment and activity level into account. The body condition managing device 10E is hence capable of even more precisely determining whether or not the user has taken the medicine.

The body condition managing device 10C described in Embodiment 4 and the body condition managing device 10D described in Embodiment 5 may retrieve a plurality of first biological data patterns and a plurality of second biological data patterns from biological data pattern groups to collate biological data with the retrieved biological data patterns.

For instance, when two first biological data patterns and two second biological data patterns have been retrieved, the collating unit 111 determines to which one of the following categories (1) to (3) the acquired biological data belongs: (1) the acquired biological data falls in the range between the two first biological data patterns (one of the first biological data patterns is taken as an upper limit of the range, and the other is taken as a lower limit); (2) the acquired biological data falls in the range between the two second biological data patterns (one of the second biological data patterns is taken as an upper limit of the range, and the other is taken as a lower limit); or (3) the acquired biological data falls outside the two ranges. If the biological data falls in one of the ranges, the collating unit 111 outputs that information to the decision-making unit 112 as a result of the collation. If the biological data falls outside the two ranges, the collating unit 111 acquires biological data again after a prescribed period of time and repeats the same process.

In Embodiments 4 and 5, the biological data patterns in the biological data pattern groups are associated with temperature and METs respectively. Embodiments 4 and 5 are not limited to such an example. For instance, the biological data pattern groups may include a plurality of biological data patterns associated with an attribute of the user. When this is the case, biological data patterns are selected for use in the collating unit 111, on the basis of, for example, an attribute (e.g., age, body height, body weight, or gender) inputted by the user on an input unit (not shown).

Software Implementation

The control blocks of the body condition managing devices 10 and 10A to 10D (particularly, the control units 11 and 11A to 11D) may be implemented by logic circuits (hardware) fabricated, for example, in the form of an integrated circuit (IC chip) and may be implemented by software executed by a CPU (central processing unit).

In the latter form of implementation, the body condition managing devices 10 and 10A to 10D each includes, among others: a CPU that executes instructions from programs or software by which various functions are implemented; a ROM (read-only memory) or like storage device (referred to as a "storage medium") containing the programs and various data in a computer-readable (or CPU-readable) format; and a RAM (random access memory) into which the programs are loaded. The computer (or CPU) then retrieves and runs the programs contained in the storage medium, thereby achieving the object of an aspect of the present disclosure. The storage medium may be a "non-transient, tangible medium" such as a tape, a disc/disk, a card, a semiconductor memory, or programmable logic circuitry. The programs may be supplied to the computer via any transmission medium (e.g., over a communications network or by broadcasting waves) that can transmit the programs. The present disclosure, in an aspect thereof, encompasses data signals on a carrier wave that are generated during electronic transmission of the programs.

Summation

The present disclosure, in aspect 1 thereof, is directed to a body condition managing device connected in a communicable manner to a biological data acquisition unit that acquires biological data representing a condition of a living body, the body condition managing device including: a collating unit configured to collate (1) the biological data acquired by the biological data acquisition unit and (2) a first biological data pattern and a second biological data pattern both being prepared in advance, the first biological data pattern representing temporal drifting of the biological data that occurs after the living body ingests a prescribed ingestible object to be ingested into the living body and the second biological data pattern representing temporal drifting of the biological data that occurs after the living body fails to ingest the ingestible object at a timing at which the living body should ingest the ingestible object; and an output unit configured to output, based on a result of the collation performed by the collating unit, information on whether or not the living body has ingested the ingestible object.

According to this configuration, information on whether or not a living body has ingested a prescribed ingestible object is outputted in accordance with a result of the collation of biological data and first and second biological data patterns. The biological data is acquired by a biological data acquisition unit. The first biological data pattern represents temporal changes of the biological data that occur after the prescribed ingestible object is ingested. The second biological data pattern represents temporal changes of the biological data that occur after the prescribed ingestible object is not ingested at a timing at which the living body should ingest the ingestible object. Hence, the body condition managing device, even when the living body is expected to manually ingest the ingestible object, is capable of determining whether or not the living body has ingested the ingestible object, without having to receive ingestion records or like inputs from the user of the body condition managing device. The body condition managing device is therefore capable of managing the manual ingestion (and failure of manual ingestion) of the ingestible object by the living body without making the user feel bothered.

The ingestible object is, for example, a medicine or food. Ingestion may be oral or non-oral, including percutaneous absorption and administration via a syringe. The living body may be the user of the body condition managing device or someone other than the user. Accordingly, the manual ingestion of the ingestible object by the living body conceptually includes the user himself/herself manually ingesting the ingestible object and the user manually causing a living body to ingest the ingestible object.

In aspect 2 of the present disclosure, the body condition managing device of aspect 1 may be configured so as to further include a time acquisition unit configured to acquire time information representing a scheduled time at which the living body is scheduled to ingest the ingestible object, wherein the first biological data pattern represents temporal drifting of the biological data that occurs after the living body ingests the ingestible object at the scheduled time, the second biological data pattern represents temporal drifting of the biological data that occurs after the living body fails to ingest the ingestible object at the scheduled time, and the collating unit collates the first and second biological data patterns and the biological data acquired by the biological data acquisition unit at a prescribed timing that comes after the scheduled time.

According to this configuration, it is determined whether or not the living body has ingested the ingestible object, by collating the biological data with the first and second biological data patterns. The biological data is acquired at a prescribed timing that comes after the scheduled time. The first biological data pattern represents temporal changes of the biological data that occur after the ingestible object is ingested at the scheduled time. The second biological data pattern represents temporal changes of the biological data that occur after the ingestible object is not ingested at the scheduled time. In other words, the biological data is acquired by using the scheduled time as a reference, and the first and second biological data patterns start at the scheduled time. Therefore, if the biological data is acquired at a prescribed timing, the body condition managing device needs only to acquire the biological data in order to determine which data points on the first and second biological data patterns the biological data matches. Thus, the body condition managing device is capable of determining whether or not the user has ingested the ingestible object, by relying on a smaller amount of biological data.

In aspect 3 of the present disclosure, the body condition managing device of aspect 1 or 2 may be configured such that the output unit outputs a warning prompting the living body to ingest the ingestible object if the result of the collation performed by the collating unit indicates that the living body has failed to ingest the ingestible object.

According to this configuration, if the living body has failed to ingest the ingestible object, a warning prompting the living body to ingest the ingestible object is outputted, which ensures the ingestion of the ingestible object by the living body. In other words, the body condition managing device is capable of managing the ingestion such that the living body does not fail to ingest the ingestible object.

In aspect 4 of the present disclosure, the body condition managing device of aspect 3 may be configured such that the output unit outputs different types of warnings depending on whether or not the biological data acquired by the biological data acquisition unit exceeds at least one prescribed threshold.

According to this configuration, the body condition managing device changes warning types in accordance with whether or not the biological data exceeds a prescribed threshold, which enables the user to easily understand the degree of urgency when the living body has failed to ingest the ingestible object. In other words, the user can easily understand whether or not the living body should immediately ingest the ingestible object.

In aspect 5 of the present disclosure, the body condition managing device of any one of aspects 1 to 4 may be configured so as to further include an update unit configured to update the first and second biological data patterns in accordance with the condition of the living body from which the biological data is acquired.

According to this configuration, the first and second biological data patterns are updated in accordance with the condition of the living body from which the biological data is acquired. Therefore, it can be accurately determined whether or not the living body has ingested the ingestible object even if the data related to the living body shows any change.

The condition of a living body may be determined based on the biological data acquired by the biological data acquisition unit and may alternatively be, for example, the living body's age, body height, body weight, or gender.

In aspect 6 of the present disclosure, the body condition managing device of any one of aspects 1 to 5 may be configured such that the body condition managing device is connected in a communicable manner to an environmental data acquisition unit that acquires environmental data representing a surrounding environment of the living body and further includes a first selection unit configured to select the first and second biological data patterns that match the environmental data acquired by the environmental data acquisition unit respectively from a plurality of first biological data patterns representing temporal drifting of the biological data in different environments and a plurality of second biological data patterns representing temporal drifting of the biological data in different environments, wherein the collating unit collates the biological data acquired by the biological data acquisition unit and the first and second biological data patterns selected by the first selection unit.

According to this configuration, the first and second biological data patterns selected from a plurality of first biological data patterns and a plurality of second biological data patterns in accordance with the acquired environmental data are collated with the acquired biological data. Specifically, the body condition managing device determines whether or not the living body has ingested the ingestible object, on the basis of the living body's biological data and surrounding environment. The body condition managing device is therefore capable of more precisely determining whether or not the living body has ingested the ingestible object.

In aspect 7 of the present disclosure, the body condition managing device of any one of aspects 1 to 6 may be configured such that the body condition managing device is connected in a communicable manner to an activity data acquisition unit that acquires activity data representing an activity condition of the living body and further includes a second selection unit configured to select the first and second biological data patterns that match the activity data acquired by the activity data acquisition unit respectively from a plurality of first biological data patterns representing temporal drifting of the biological data in different activity conditions and a plurality of second biological data patterns representing temporal drifting of the biological data in different activity conditions, wherein the collating unit collates the biological data acquired by the biological data acquisition unit and the first and second biological data patterns selected by the second selection unit.

According to this configuration, the first and second biological data patterns selected from a plurality of first biological data patterns and a plurality of second biological data patterns in accordance with the acquired activity data are collated with the acquired biological data. Specifically, the body condition managing device determines whether or not the living body has ingested the ingestible object, on the basis of the living body's biological data and activity condition. The body condition managing device is therefore capable of more precisely determining whether or not the living body has ingested the ingestible object.

The present disclosure, in aspect 8 thereof, is directed to a body condition managing method including: the biological data acquisition step of acquiring biological data representing a condition of a living body; the collating step of collating (1) the biological data acquired in the biological data acquisition step and (2) a first biological data pattern and a second biological data pattern both being prepared in advance, the first biological data pattern representing temporal drifting of the biological data that occurs after the living body ingests a prescribed ingestible object to be ingested into the living body and the second biological data pattern representing temporal drifting of the biological data that occurs after the living body fails to ingest the ingestible object at a timing at which the living body should ingest the ingestible object; and the output step of outputting, based on a result of the collation performed in the collating step, information on whether or not the living body has ingested the ingestible object.

According to the method, the body condition managing device, even when the living body is expected to manually ingest the ingestible object, is capable of determining whether or not the living body has ingested the ingestible object, without having to receive ingestion records or like inputs from the user of the body condition managing device, similarly to the body condition managing device of aspect 1 of the present disclosure. The body condition managing device is therefore capable of managing the manual ingestion (and failure of manual ingestion) of the ingestible object by the living body without making the user feel bothered.

The body condition managing device of any aspect of the present disclosure may be implemented on a computer, in which case the present disclosure encompasses a control program that causes a computer to function as the various units (software elements) of the body condition managing device, thereby implementing the body condition managing device on the computer, and also encompasses a computer-readable storage medium containing the control program.

The present disclosure, in any aspect thereof, is not limited to the description of the embodiments above and may be altered within the scope of the claims. Embodiments based on a proper combination of technical means disclosed in different embodiments are encompassed in the technical scope of the aspect of the present disclosure. Furthermore, a new technological feature can be created by combining different technological means disclosed in the embodiments.

CROSS-REFERENCE TO RELATED APPLICATIONS

The present application claims the benefit of priority to Japanese Patent Application, Tokugan, No. 2017-122612 filed on Jun. 22, 2017, the entire contents of which are incorporated herein by reference.

REFERENCE SIGNS LIST 10, 10A, 10B, 10C, 10D Body Condition Managing Device
20 Biosensor (Biological Data Acquisition Unit)
40 Environmental Sensor (Environmental Data Acquisition Unit)
50 Activity Level Meter (Activity Data Acquisition Unit)
111 Collating Unit
113 Warning Output Unit (Output Unit)
114 Update Unit
115 Scheduled Time Acquisition Unit (Time Acquisition Unit)
116 Pattern Selection Unit (First Selection Unit)
117 Pattern Selection Unit (Second Selection Unit)

The invention claimed is:

1. A body condition managing device connected in a communicable manner to a sensor that acquires biological data representing a condition of a living body, the body condition managing device comprising:
a collating circuit configured to collate (1) the biological data acquired by the sensor and (2) a first biological data pattern and a second biological data pattern both being prepared in advance, the first biological data pattern representing temporal drifting of the biological data that occurs after the living body ingests a prescribed ingestible object to be ingested into the living body and the second biological data pattern representing temporal drifting of the biological data that occurs after the living body fails to ingest the ingestible object at a timing at which the living body should ingest the ingestible object;
a first selection circuit that communicates with an environmental sensor; and
an output circuit configured to output, based on a result of the collation performed by the collating circuit, information on whether or not the living body has ingested the ingestible object, wherein
the collating circuit causes the sensor to acquire the biological data at a time when a significant difference is found between the first biological data pattern and the second biological data pattern, in cases where the prescribed ingestible object is ingested by the living body and where the prescribed ingestible object is not ingested by the living body,
the collating circuit acquires, at least once, the biological data acquired by the sensor at the time,
the first selection circuit controls the environmental sensor to acquire environmental data representing temperature or humidity in surroundings of the living body, or information on weather in a geographical area of the living body,
the first selection circuit is configured to, as the first and second biological data patterns, select first and second biological data patterns that match the environmental data acquired by the environmental sensor respectively from a plurality of first biological data patterns representing temporal drifting of the biological data in different environments and a plurality of second biological data patterns representing temporal drifting of the biological data in different environments,
the collating circuit collates the biological data acquired by the sensor and the first and second biological data patterns selected by the first selection circuit, and
the body condition managing device further includes an update circuit configured to update the first and second biological data patterns based on the biological data or an attribute of the living body.

2. The body condition managing device according to claim 1, further comprising a time acquisition circuit configured to acquire time information representing a scheduled time at which the living body is scheduled to ingest the ingestible object, wherein
the first biological data pattern represents temporal drifting of the biological data that occurs after the living body ingests the ingestible object at the scheduled time,
the second biological data pattern represents temporal drifting of the biological data that occurs after the living body fails to ingest the ingestible object at the scheduled time, and
the collating circuit collates the first and second biological data patterns and the biological data acquired by the sensor at a prescribed timing that comes after the scheduled time.

3. The body condition managing device according to claim 1, wherein the output circuit outputs a warning prompting the living body to ingest the ingestible object if the result of the collation performed by the collating circuit indicates that the living body has failed to ingest the ingestible object.

4. The body condition managing device according to claim 3, wherein the output circuit outputs different types of warnings depending on whether or not the biological data acquired by the sensor exceeds at least one prescribed threshold.

5. The body condition managing device according to claim 1, the body condition managing device being connected in a communicable manner to an activity data acquisition circuit that acquires activity data representing an activity condition of the living body and further comprising a second selection circuit configured to select, as the first and second biological data patterns, first and second biological data patterns that match the activity data acquired by the activity data acquisition circuit respectively from a plurality of first biological data patterns representing temporal drifting of the biological data in different activity conditions and a plurality of second biological data patterns representing temporal drifting of the biological data in different activity conditions, wherein
the collating circuit collates the biological data acquired by the sensor and the first and second biological data patterns selected by the second selection circuit.

6. The body condition managing device according to claim 2, wherein the output circuit outputs a warning prompting the living body to ingest the ingestible object if the result of the collation performed by the collating circuit indicates that the living body has failed to ingest the ingestible object.

7. The body condition managing device according to claim 6, wherein the output circuit outputs different types of warnings depending on whether or not the biological data acquired by the sensor exceeds at least one prescribed threshold.

8. A body condition managing method comprising:
a biological data acquisition step of acquiring biological data representing a condition of a living body;
a control step of communicating with an environmental sensor to control the environmental sensor to acquire environmental data representing temperature or humidity in surroundings of the living body, or information on weather in a geographical area of the living body;
a selection step of selecting, as a first data pattern and a second biological data pattern, first and second biological data patterns that match the environmental data acquired by the environmental sensor respectively from a plurality of first biological data patterns representing temporal drifting of the biological data in different environments and a plurality of second biological data patterns representing temporal drifting of the biological data in different environments;
a collating step of collating (1) the biological data acquired in the biological data acquisition step and (2) the first biological data pattern and the second biological data pattern both being prepared in advance, the first biological data pattern representing temporal drifting of the biological data that occurs after the living body ingests a prescribed ingestible object to be ingested into the living body and the second biological data pattern representing temporal drifting of the biological data that occurs after the living body fails to ingest the ingestible object at a timing at which the living body should ingest the ingestible object; and
an output step of outputting, based on a result of the collation performed in the collating step, information on whether or not the living body has ingested the ingestible object, wherein
the collating step causes the biological data acquired in the biological data acquisition step to be acquired at a time when a significant difference is found between the first biological data pattern and the second biological data pattern, in cases where the prescribed ingestible object is ingested by the living body and where the prescribed ingestible object is not ingested by the living body,
the collating step acquires, at least once, the biological data acquired by the biological data acquisition step at the time,
the collating step collates the biological data acquired in the communication step and the first and second biological data patterns selected in the selection step, and
the body condition managing method further includes an updating step of updating the first and second biological data patterns based on the biological data or an attribute of the living body.

* * * * *